(12) United States Patent
Nguyen et al.

(10) Patent No.: US 7,650,887 B2
(45) Date of Patent: Jan. 26, 2010

(54) WOUND RETRACTOR

(75) Inventors: Eric Nguyen, Corona, CA (US); Donald L. Gadberry, San Juan Capistrano, CA (US); Gary M. Johnson, Mission Viejo, CA (US); Charles C. Hart, Summerville, SC (US); John R. Brustad, Dana Point, CA (US); Robert R. Bowes, II, Laguna Hills, CA (US); Jeremy J. Albrecht, Ladera Ranch, CA (US); Ghassan Sakakine, Rancho Santa Margarita, CA (US); Henry Kahle, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 193 days.

(21) Appl. No.: 10/516,198

(22) PCT Filed: Jun. 3, 2003

(86) PCT No.: PCT/US03/17389

§ 371 (c)(1),
(2), (4) Date: Nov. 30, 2004

(87) PCT Pub. No.: WO03/103548

PCT Pub. Date: Dec. 18, 2003

(65) Prior Publication Data

US 2005/0241647 A1 Nov. 3, 2005

Related U.S. Application Data

(60) Provisional application No. 60/386,159, filed on Jun. 5, 2002, provisional application No. 60/415,351, filed on Oct. 2, 2002.

(51) Int. Cl.
*A61F 13/00* (2006.01)
(52) U.S. Cl. .................................. 128/888; 128/889
(58) Field of Classification Search ............... 128/845, 128/846, 888, 889; 602/42–43, 50, 60, 63, 602/75, 901
See application file for complete search history.

(56) References Cited

U.S. PATENT DOCUMENTS 558,364 A 4/1896 Doolittle (Continued)

FOREIGN PATENT DOCUMENTS

EP 1 125 552 8/2001

(Continued)

OTHER PUBLICATIONS

Dexterity Protractor Instruction Manual by Dexterity Surgical, Inc.

(Continued)

*Primary Examiner*—Michael A. Brown
(74) *Attorney, Agent, or Firm*—Pui Tong Ho; David G. Majdali; Kenneth K. Vu

(57) ABSTRACT

An incrementally adjustable wound retractor (100), having a first ring (102) with a diameter greater than the desired diameter of the wound incision. A second ring (104), having an annular axis and a diameter greater than the desired diameter of the wound incision. A flexible sleeve (106), disposed in a generally cylindrical form between the first and second rings (102, 104), the second ring may be rolled over itself and around the annular axis to provide a sleeve with a radical retraction force sufficient to stretch the incision to the desired diameter.

30 Claims, 32 Drawing Sheets

U.S. PATENT DOCUMENTS

| | | | |
|---|---|---|---|
| 1,157,202 | A | 10/1915 | Bates et al. |
| 1,810,466 | A | 6/1931 | Deutsch |
| 2,305,289 | A | 12/1942 | Coburg |
| 2,478,586 | A | 8/1949 | Krapp |
| 2,812,758 | A | 11/1957 | Blumenschein |
| 2,835,253 | A | 5/1958 | Borgeson |
| 2,853,075 | A | 9/1958 | Hoffman et al. |
| 3,039,468 | A | 6/1962 | Price |
| 3,111,943 | A | 11/1963 | Orndorff |
| 3,195,934 | A | 7/1965 | Parrish |
| 3,244,169 | A | 4/1966 | Baxter |
| 3,332,417 | A | 7/1967 | Blanford et at. |
| 3,347,226 | A | 10/1967 | Harrower |
| 3,347,227 | A * | 10/1967 | Harrower .................... 128/850 |
| 3,397,692 | A | 8/1968 | Creager, Jr. et al. |
| 3,402,710 | A | 9/1968 | Paleschuck |
| 3,416,520 | A | 12/1968 | Creager, Jr. |
| 3,447,533 | A | 6/1969 | Spicer |
| 3,523,534 | A | 8/1970 | Nolan |
| 3,717,151 | A | 2/1973 | Collett |
| 3,831,583 | A | 8/1974 | Edmunds et al. |
| 3,841,332 | A | 10/1974 | Treacle |
| 3,850,172 | A | 11/1974 | Cazalis |
| 3,856,021 | A | 12/1974 | McIntosh |
| 3,860,274 | A | 1/1975 | Ledstrom et al. |
| 4,024,872 | A | 5/1977 | Muldoon |
| 4,043,328 | A | 8/1977 | Cawood, Jr. et al. |
| 4,069,913 | A | 1/1978 | Harrigan |
| 4,083,370 | A | 4/1978 | Taylor |
| 4,188,945 | A | 2/1980 | Wenander |
| 4,217,664 | A | 8/1980 | Faso |
| 4,222,126 | A | 9/1980 | Boretos et al. |
| 4,254,973 | A | 3/1981 | Benjamin |
| 4,338,937 | A | 7/1982 | Lerman |
| 4,367,728 | A | 1/1983 | Mutke |
| 4,369,284 | A | 1/1983 | Chen |
| 4,454,873 | A | 6/1984 | Laufenberg et al. |
| 4,475,548 | A | 10/1984 | Muto |
| 4,550,713 | A | 11/1985 | Hyman |
| 4,553,537 | A | 11/1985 | Rosenberg |
| 4,691,942 | A | 9/1987 | Ford |
| 4,714,749 | A | 12/1987 | Hughes et al. |
| 4,755,170 | A | 7/1988 | Golden |
| 4,777,943 | A | 10/1988 | Chvapil |
| 4,798,594 | A | 1/1989 | Hillstead |
| 4,802,694 | A | 2/1989 | Vargo |
| 4,842,931 | A | 6/1989 | Zook |
| 4,856,502 | A | 8/1989 | Ersfeld et al. |
| 4,863,438 | A | 9/1989 | Gauderer et al. |
| 4,889,107 | A | 12/1989 | Kaufman |
| 4,895,565 | A | 1/1990 | Hillstead |
| 4,903,710 | A | 2/1990 | Jessamine et al. |
| 4,911,974 | A | 3/1990 | Shimizu et al. |
| 4,926,882 | A | 5/1990 | Lawrence |
| 4,950,223 | A | 8/1990 | Silvanov |
| 4,984,564 | A | 1/1991 | Yuen |
| 4,991,593 | A | 2/1991 | LeVahn |
| 4,998,538 | A | 3/1991 | Charowsky et al. |
| 5,009,224 | A | 4/1991 | Cole |
| 5,015,228 | A | 5/1991 | Columbus et al. |
| 5,037,379 | A | 8/1991 | Clayman et al. |
| 5,082,005 | A | 1/1992 | Kaldany |
| 5,159,921 | A | 11/1992 | Hoover |
| 5,178,162 | A | 1/1993 | Bose |
| 5,192,301 | A | 3/1993 | Kamiya et al. |
| 5,207,656 | A | 5/1993 | Kranys |
| 5,213,114 | A | 5/1993 | Bailey, Jr. |
| 5,259,366 | A | 11/1993 | Reydel et al. |
| 5,262,468 | A | 11/1993 | Chen |
| 5,299,582 | A | 4/1994 | Potts |
| 5,316,541 | A | 5/1994 | Fischer |
| 5,336,708 | A | 8/1994 | Chen |
| 5,350,364 | A | 9/1994 | Stephens et al. |
| 5,353,786 | A | 10/1994 | Wilk |
| 5,366,478 | A | 11/1994 | Brinkerhoff et al. |
| 5,368,545 | A | 11/1994 | Schaller et al. |
| 5,380,288 | A | 1/1995 | Hart |
| 5,389,080 | A | 2/1995 | Yoon |
| 5,389,081 | A | 2/1995 | Castro |
| 5,407,433 | A | 4/1995 | Loomas |
| 5,429,609 | A | 7/1995 | Yoon |
| 5,437,683 | A | 8/1995 | Neumann et al. |
| 5,441,486 | A | 8/1995 | Yoon |
| 5,456,284 | A | 10/1995 | Ryan et al. |
| 5,460,616 | A | 10/1995 | Weinstein |
| 5,476,475 | A | 12/1995 | Gadberry |
| 5,480,410 | A | 1/1996 | Cuschieri et al. |
| 5,486,426 | A | 1/1996 | McGee et al. |
| 5,492,304 | A | 2/1996 | Smith |
| 5,496,280 | A | 3/1996 | Vandenbroek |
| 5,503,112 | A | 4/1996 | Luhman et al. |
| 5,508,334 | A | 4/1996 | Chen |
| 5,514,133 | A | 5/1996 | Golub et al. |
| 5,518,278 | A | 5/1996 | Sampson |
| 5,522,791 | A | 6/1996 | Leyva |
| 5,524,644 | A * | 6/1996 | Crook ...................... 128/888 |
| 5,531,758 | A | 7/1996 | Uschold |
| 5,545,179 | A | 8/1996 | Williamson, IV |
| 5,562,677 | A | 10/1996 | Hildwein et al. |
| 5,603,702 | A | 2/1997 | Smith |
| 5,628,732 | A | 5/1997 | Antoon, Jr. |
| 5,632,284 | A | 5/1997 | Graether |
| 5,634,911 | A | 6/1997 | Hermann et al. |
| 5,634,936 | A | 6/1997 | Linden et al. |
| 5,634,937 | A | 6/1997 | Mollenauer et al. |
| 5,636,645 | A | 6/1997 | Ou |
| 5,640,977 | A | 6/1997 | Leahy et al. |
| 5,649,550 | A | 7/1997 | Crook |
| 5,653,705 | A | 8/1997 | de la Torre et al. |
| 5,672,168 | A | 9/1997 | de la Torre et al. |
| 5,681,341 | A | 10/1997 | Lunsford et al. |
| 5,709,664 | A | 1/1998 | Vandenbroek |
| 5,720,730 | A | 2/1998 | Blake, III |
| 5,728,103 | A | 3/1998 | Picha et al. |
| 5,741,298 | A | 4/1998 | MacLeod |
| 5,753,150 | A | 5/1998 | Martin et al. |
| 5,782,817 | A | 7/1998 | Franzel |
| 5,788,676 | A | 8/1998 | Yoon |
| 5,792,119 | A | 8/1998 | Marx |
| 5,795,290 | A | 8/1998 | Bridges |
| 5,803,919 | A | 9/1998 | Hart et al. |
| 5,803,921 | A | 9/1998 | Bonadio |
| 5,803,923 | A | 9/1998 | Singh-Derewa et al. |
| 5,810,721 | A | 9/1998 | Mueller et al. |
| 5,813,409 | A | 9/1998 | Leahy et al. |
| 5,814,026 | A | 9/1998 | Yoon |
| 5,819,375 | A | 10/1998 | Kastner |
| 5,832,925 | A | 11/1998 | Rothrum |
| 5,841,298 | A | 11/1998 | Huang |
| 5,853,395 | A | 12/1998 | Crook et al. |
| 5,865,729 | A | 2/1999 | Meehan et al. |
| 5,865,807 | A | 2/1999 | Blake, III |
| 5,871,474 | A | 2/1999 | Hermann |
| 5,895,377 | A | 4/1999 | Smith |
| 5,899,208 | A | 5/1999 | Bonadio |
| 5,904,703 | A | 5/1999 | Gilson |
| 5,906,577 | A | 5/1999 | Beane et al. |
| 5,919,476 | A | 7/1999 | Fischer et al. |
| 5,947,922 | A | 9/1999 | MacLeod |
| 5,951,588 | A | 9/1999 | Moenning |
| 5,957,888 | A | 9/1999 | Hinchliffe |
| 5,957,913 | A | 9/1999 | de la Torre |
| 5,962,572 | A | 10/1999 | Chen |
| 5,964,781 | A | 10/1999 | Mollenauer et al. |

| | | | | | | |
|---|---|---|---|---|---|---|
| 5,989,233 A | 11/1999 | Yoon | | 2003/0192553 A1 | 10/2003 | Rambo |
| 5,989,266 A | 11/1999 | Foster | | 2003/0225392 A1 | 12/2003 | McMichael et al. |
| 5,993,471 A | 11/1999 | Riza | | 2004/0015185 A1 | 1/2004 | Ewers et al. |
| 5,993,485 A | 11/1999 | Beckers | | 2004/0024363 A1 | 2/2004 | Goldberg |
| 5,997,515 A | 12/1999 | de la Torre et al. | | 2004/0049099 A1 | 3/2004 | Ewers et al. |
| 6,010,494 A | 1/2000 | Schafer | | 2004/0049100 A1 | 3/2004 | Butler et al. |
| 6,024,736 A | 2/2000 | de la Torre et al. | | 2004/0054353 A1 | 3/2004 | Taylor |
| 6,025,067 A | 2/2000 | Fay | | 2004/0073090 A1 | 4/2004 | Butler et al. |
| 6,033,426 A | 3/2000 | Kaji | | 2004/0092796 A1 | 5/2004 | Butler et al. |
| 6,033,428 A | 3/2000 | Sardella | | 2004/0106942 A1 | 6/2004 | Taylor |
| 6,035,559 A | 3/2000 | Freed et al. | | 2004/0127772 A1 | 7/2004 | Ewers et al. |
| 6,045,535 A | 4/2000 | Ben Nun | | 2004/0154624 A1 | 8/2004 | Bonadio et al. |
| 6,053,934 A | 4/2000 | Andrews | | 2004/0167559 A1 | 8/2004 | Taylor et al. |
| 6,077,288 A | 6/2000 | Shimomura | | 2004/0173218 A1 | 9/2004 | Yamada et al. |
| 6,090,043 A | 7/2000 | Austin et al. | | 2004/0215063 A1 | 10/2004 | Bonadio et al. |
| 6,110,154 A | 8/2000 | Shimomura et al. | | 2004/0254426 A1 | 12/2004 | Wenchell |
| 6,142,935 A | 11/2000 | Flom | | 2004/0267096 A1 | 12/2004 | Caldwell et al. |
| 6,142,936 A | 11/2000 | Beane et al. | | 2005/0020884 A1 | 1/2005 | Hart et al. |
| 6,149,642 A | 11/2000 | Gerhart et al. | | 2005/0033246 A1 | 2/2005 | Ahlberg et al. |
| 6,150,608 A | 11/2000 | Wambeke et al. | | 2005/0059865 A1 | 3/2005 | Kahle et al. |
| 6,162,172 A | 12/2000 | Cosgrove et al. | | 2005/0090717 A1 | 4/2005 | Bonadio et al. |
| 6,224,612 B1 | 5/2001 | Bates | | 2005/0148823 A1 | 7/2005 | Vaugh et al. |
| 6,238,373 B1 | 5/2001 | de la Torre | | 2005/0155611 A1 | 7/2005 | Vaugh et al. |
| 6,254,533 B1 | 7/2001 | Fadem et al. | | 2005/0197537 A1 | 9/2005 | Bonadio et al. |
| 6,254,534 B1* | 7/2001 | Butler et al. ............... 600/208 | | 2005/0222582 A1 | 10/2005 | Wenchell |
| 6,276,661 B1 | 8/2001 | Laird | | 2005/0241647 A1 | 11/2005 | Nguyen |
| 6,287,280 B1 | 9/2001 | Lampropoulos | | 2005/0261720 A1 | 11/2005 | Caldwell et al. |
| 6,319,246 B1 | 11/2001 | de la Torre | | 2005/0267419 A1 | 12/2005 | Smith et al. |
| 6,325,384 B1 | 12/2001 | Berry, Sr. et al. | | 2005/0283050 A1 | 12/2005 | Gundlappalii et al. |
| 6,382,211 B1* | 5/2002 | Crook ...................... 128/849 | | 2005/0288558 A1 | 12/2005 | Ewers et al. |
| 6,383,162 B1 | 5/2002 | Sugarbaker | | 2006/0030755 A1 | 2/2006 | Ewers et al. |
| 6,413,244 B1 | 7/2002 | Bestetti | | 2006/0047284 A1 | 3/2006 | Gresham |
| 6,440,063 B1 | 8/2002 | Beane et al. | | 2006/0052669 A1 | 3/2006 | Hart |
| 6,450,983 B1 | 9/2002 | Rambo | | 2006/0084842 A1 | 4/2006 | Hart et al. |
| 6,482,181 B1 | 11/2002 | Racenet | | 2006/0129165 A1 | 6/2006 | Edoga et al. |
| 6,485,435 B1 | 11/2002 | Bakal | | 2006/0149137 A1* | 7/2006 | Pingleton et al. ............ 600/208 |
| 6,533,734 B1 | 3/2003 | Corley, III et al. | | 2006/0149306 A1 | 7/2006 | Hart et al. |
| 6,551,344 B2 | 4/2003 | Thill | | 2006/0161050 A1 | 7/2006 | Butler et al. |
| 6,578,577 B2 | 6/2003 | Bonadio et al. | | | | |
| 6,579,281 B2 | 6/2003 | Palmer et al. | | FOREIGN PATENT DOCUMENTS | | |
| 6,582,364 B2 | 6/2003 | Butler et al. | | IE | S940150 | 10/1950 |
| 6,589,167 B1 | 7/2003 | Shimomura et al. | | IE | 930649 | 9/1993 |
| 6,589,211 B1 | 7/2003 | Macleod | | IE | 930650 | 9/1993 |
| 6,613,952 B2 | 9/2003 | Rambo | | IE | S940150 | 2/1994 |
| 6,623,426 B2 | 9/2003 | Bonadio et al. | | IE | S940613 | 8/1994 |
| 6,702,787 B2 | 3/2004 | Racenet et al. | | IE | S940960 | 12/1994 |
| 6,723,044 B2* | 4/2004 | Pulford et al. ............. 600/208 | | IE | S950055 | 7/1996 |
| 6,814,078 B2 | 11/2004 | Crook et al. | | IE | S71634 | 2/1997 |
| 6,846,287 B2 | 1/2005 | Bonadio et al. | | IE | S950266 | 2/1997 |
| 6,866,861 B1 | 3/2005 | Luhman | | IE | S75368 | 8/1997 |
| 6,895,965 B2 | 5/2005 | Scarberry et al. | | IE | S960196 | 8/1997 |
| 6,902,541 B2 | 6/2005 | McNally et al. | | IE | S970810 | 11/1997 |
| 6,908,430 B2 | 6/2005 | Caldwell et al. | | IE | 990218 | 11/2000 |
| 6,939,296 B2 | 9/2005 | Ewers et al. | | IE | 990219 | 11/2000 |
| 6,945,932 B1 | 9/2005 | Caldwell et al. | | IE | 990220 | 11/2000 |
| 6,958,037 B2 | 10/2005 | Ewers et al. | | IE | 990660 | 2/2001 |
| 6,972,026 B1 | 12/2005 | Caldwell et al. | | IE | 990795 | 3/2001 |
| 6,997,909 B2 | 2/2006 | Goldberg | | JP | 11-290327 | 10/1999 |
| 7,033,319 B2 | 4/2006 | Pulford et al. | | JP | 2002-28163 | 1/2002 |
| 7,052,454 B2 | 5/2006 | Taylor | | JP | 02003 235879 A | 8/2003 |
| 7,081,089 B2 | 7/2006 | Bonadio et al. | | WO | WO95/07056 | 3/1995 |
| 7,214,185 B1 | 5/2007 | Rosney | | WO | WO95/22289 | 8/1995 |
| 2001/0037053 A1 | 11/2001 | Bonadio et al. | | WO | WO 95/24864 | 9/1995 |
| 2001/0047188 A1 | 11/2001 | Bonadio et al. | | WO | WO 95/27468 | 10/1995 |
| 2002/0002324 A1 | 1/2002 | McManus | | WO | WO 97/11642 | 4/1997 |
| 2002/0038077 A1 | 3/2002 | de la Torre et al. | | WO | WO 98/19853 | 5/1998 |
| 2002/0072762 A1 | 6/2002 | Bonadio et al. | | WO | WO 98/35614 | 8/1998 |
| 2002/0156432 A1 | 10/2002 | Racenet | | WO | WO 98/48724 | 11/1998 |
| 2002/0162559 A1 | 11/2002 | Crook | | WO | WO 99/15068 | 4/1999 |
| 2003/0040711 A1 | 2/2003 | Racenet et al. | | WO | WO 99/25268 | 5/1999 |
| 2003/0078478 A1 | 4/2003 | Bonadio et al. | | WO | WO 00/32116 | 6/2000 |
| 2003/0139756 A1 | 7/2003 | Brustad | | WO | WO 0035356 | 6/2000 |
| 2003/0187376 A1 | 10/2003 | Rambo | | | | |

| WO | WO 00/32120 | 8/2000 |
|---|---|---|
| WO | WO00/54676 | 9/2000 |
| WO | WO00/54677 | 9/2000 |
| WO | WO0054675 | 9/2000 |
| WO | WO01/08581 | 2/2001 |
| WO | WO 01/26559 | 4/2001 |
| WO | WO02/34108 | 5/2002 |
| WO | WO03/032819 | 4/2003 |
| WO | WO03/034908 | 5/2003 |
| WO | WO03/061480 | 7/2003 |
| WO | WO 03/077726 | 9/2003 |
| WO | WO 03/103548 | 12/2003 |
| WO | WO 2004/075730 A2 | 9/2004 |
| WO | WO 2004/075730 A3 | 9/2004 |
| WO | WO 2004/075741 A2 | 9/2004 |
| WO | WO 2004/075741 A3 | 9/2004 |
| WO | WO 2004/075930 A2 | 9/2004 |
| WO | WO 2004/075930 A3 | 9/2004 |
| WO | WO 2005/034766 A2 | 4/2005 |

OTHER PUBLICATIONS

Neil Sheehan, Supplemental Expert Report of Neil Sheehan, Re: U S. Patent No. 5,741,298, United States District Court for the Central District of California, Civil Action No. SACV 03-1322 JVS, Aug. 9, 2005.

Horigane, et al., Technical Note: Development of a Duodoenal Cannula for Sheep, Journal of Animal Science, Apr. 1992, vol. 70, Issue 4, pp. 1216-1219.

Horigane, et al., Silicone Rumen Cannula with a Soft Cylindrical Part and a Hard Flange, Journal of Dairy Science, Nov. 1989, vol. 72, No. 11, pp. 3230-3232.

McSweeney, Cannuliation of the Rumen in Cattle and Buffaloes, Australian Veterinary Journal, Aug. 1989, vol. 66, No. 8, pp. 266-268.

Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.

Co-Pending U.S. Appl. No. 10/381,220, filed Mar. 20, 2003; Title: Surgical Access Apparatus and Method.

Co-Pending U.S. Appl. No. 11/755,305, filed May 30, 2007; Title: Wound Retraction Apparatus and Method.

Co-Pending U.S. Appl. No. 10/927,551, filed Aug. 25, 2004; Title: Surgical Access System.

Co-Pending U.S. Appl. No. 11/244,647, filed Oct. 5, 2005; Title: Surgical Access Apparatus and Method.

Co-Pending U.S. Appl. No. 11/245,709, filed Oct. 7, 2005; Title: Surgical Access System.

Co-Pending U.S. Appl. No. 11/330,661, filed Jan. 12, 2006; Title: Sealed Surgical Access Device.

Co-Pending U S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.

Co-Pending U.S. Appl. No. 11/548,765, filed Oct. 12, 2006; Title: Split Hoop Wound Retractor.

Co-Pending U S. Appl. No. 11/548,767, filed Oct. 12, 2006; Title: Circular Surgical Retractor.

Co-Pending U.S. Appl. No. 11/548,781, filed Oct. 12, 2006; Title: Wound Retractor With Gel Cap.

Co-Pending U.S. Appl. No. 11/548,955, filed Oct. 12,2006; Title: Hand Access Laparoscopic Device.

Co-Pending U.S. Appl. No. 11/564,409, filed Nov. 29, 2006; Title: Surgical Instrument Access Device.

US 5,344,646, Chen (withdrawn).

Co-Pending U.S. Appl. No. 10/381,220, filed Mar. 20, 2003; Title: Surgical Access Apparatus and Method.

US Patent Office, International Search Report and The Written Opinion of the International Searching Authority for PCT Application No. PCT/US2004/05484.

European Patent Office, International Search Report and The Written Opinion of the International Searching Authority for PCT Application No. PCT/US2006/039799 mailed Mar. 27, 2007.

European Patent Office, International Search Report and The Written Opinion of the International Searching Authority for PCT Application No. PCT/US2006/039800 mailed Apr. 16, 2007.

European Patent Office, International Search Report and Written Opinion of the International Searching Authority for International Application No. PCT/US2006/039883, mailed Jan. 31, 2007.

European Patent Office, International Search Report and Written Opinion of the International Searching Authority for International Application No. PCT/US2006/039905, mailed Jan. 17, 2007.

European Patent Office, International Search Report and The Written Opinion of the International Searching Authority for International Application No. PCT/US2006/040073, Jan. 26, 2007.

European Patent Office, International Search Report and The Written Opinion of the International Searching Authority for International Application No. PCT/US2006/040154 mailed Jan. 30, 2007.

International Search Report and Written Opinion of the International Searching Authority for PCT application No. PCT/US01/29682.

Technical Note: Development of a Duodenal Cannula for Sheep, Faculty of Agriculture and Schol of Medicine Tohoku University, Sendai 981, Japan.

The International Bureau of WIPO, International Preliminary Report on Patentability, dated Aug. 29, 2006, for international application No. PCT/US2004/028250.

The International Bureau of WIPO, International Preliminary Report on Patentability dated Apr. 16, 2008 for PCT Application No. PCT/US2006/039799.

The International Bureau of WIPO, International Preliminary Report on Patentability for International Application No. PCT/US2006/039800 dated Apr. 16, 2008.

Co-Pending U.S. Appl. No. 12/108,400, filed Apr. 23, 2008; Title Wound Retraction Apparatus and Method.

European Patent Office, Supplementary European Search Report for European Patent Application No. EP 03 75 7319, based on International Application No. PCT/US03/17389, dated Jan. 19, 2009, entitled "Wound Retractor".

European Patent Office, Supplementary European Search Report for European Application No. EP 01 97 3379, dated Jul. 5, 2007, based on International Patent Application No. PCT/US01/29682, filed Sep. 21, 2001.

* cited by examiner

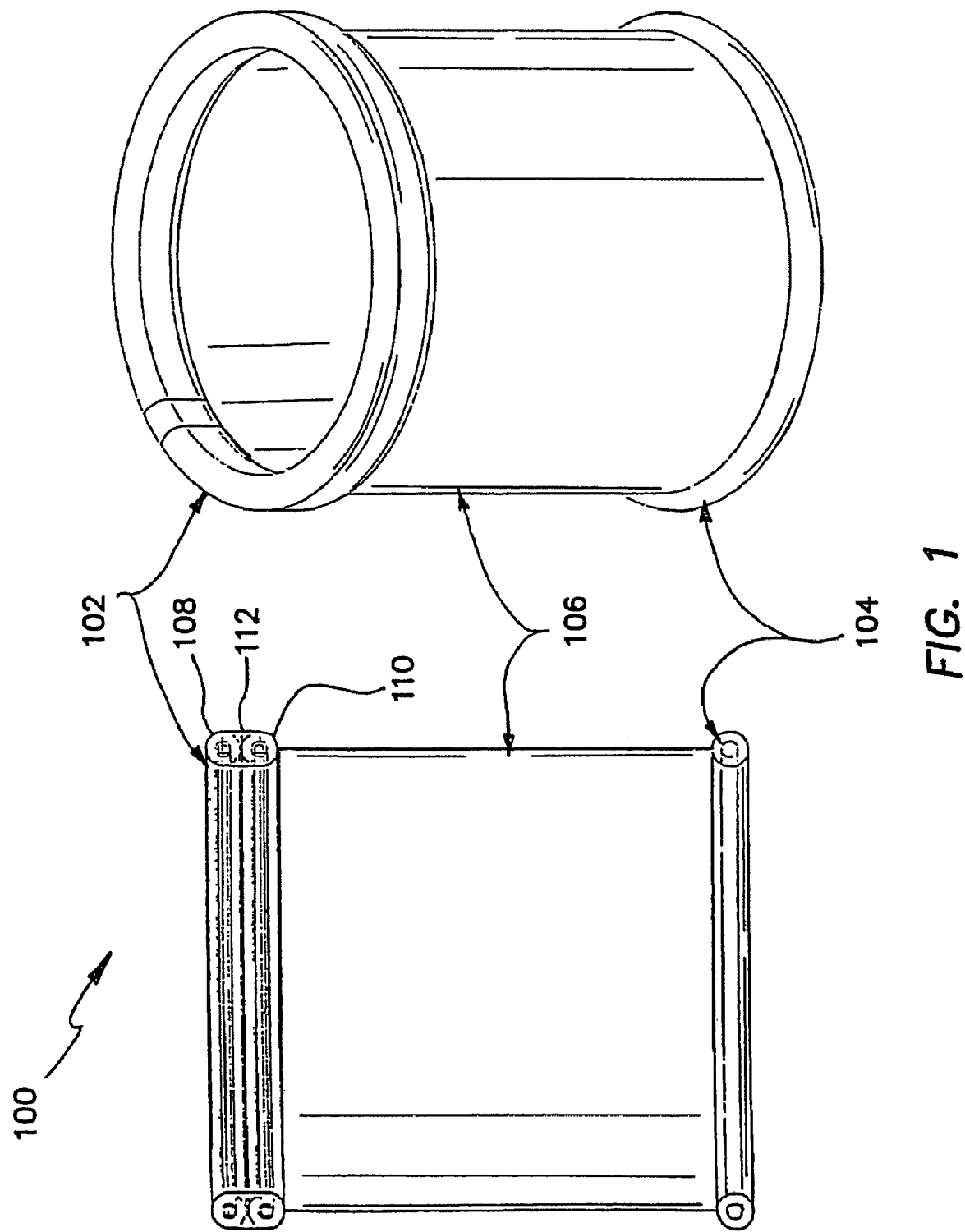

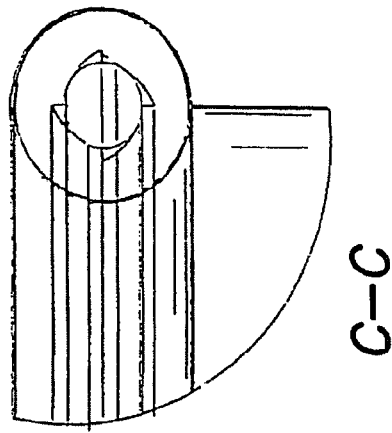
C-C
FIG. 6
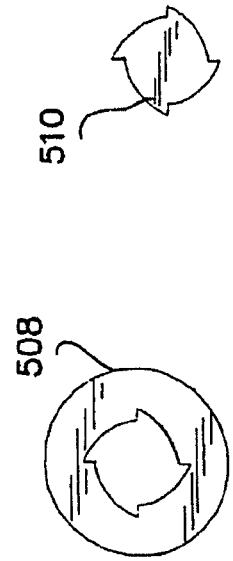
FIG. 5
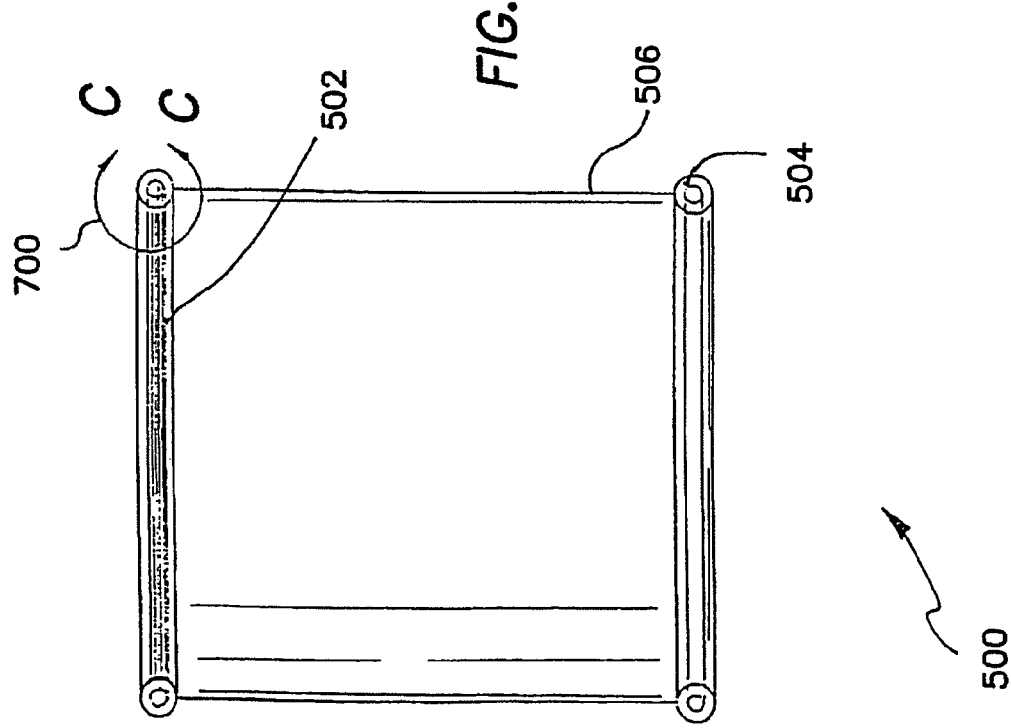
FIG. 7

510

FIG. 17e
FIG. 17d
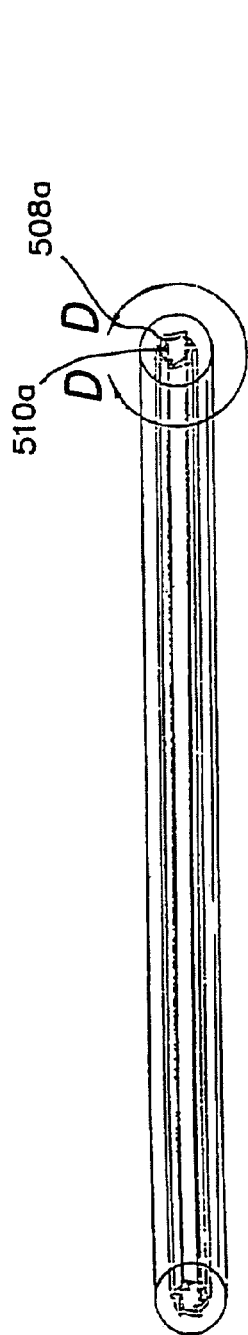
FIG. 18a
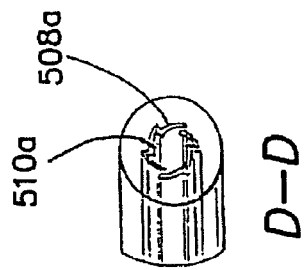
D-D

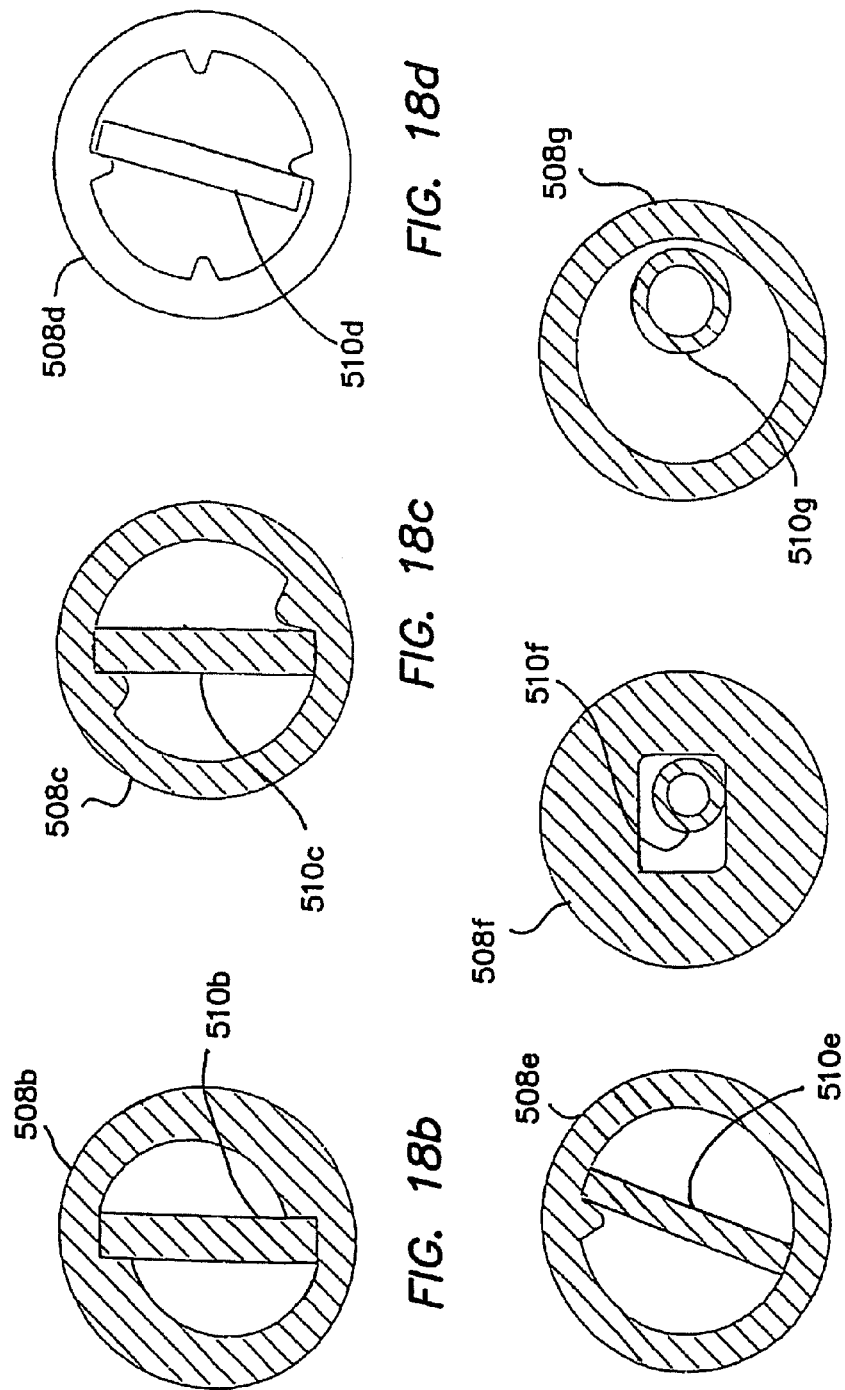

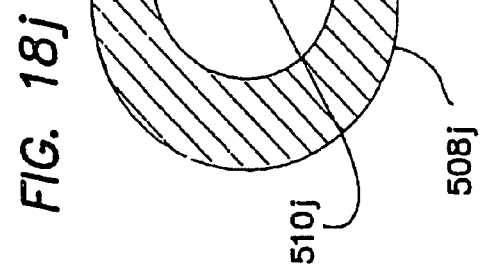
FIG. 18j
FIG. 18i
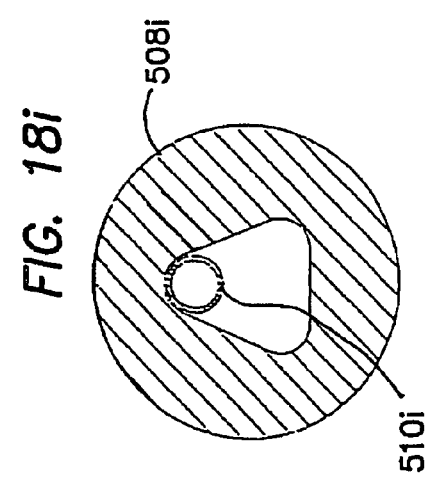
FIG. 18ℓ
FIG. 18h
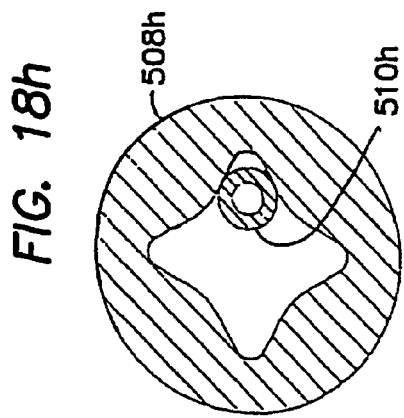
FIG. 18k
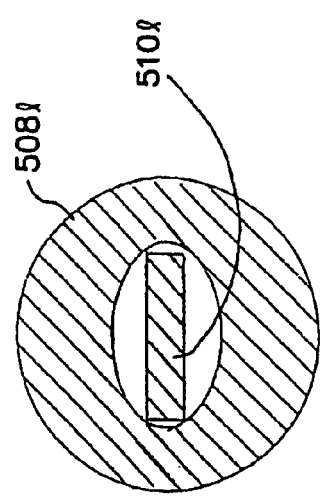
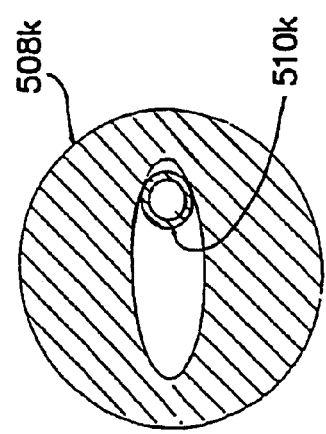

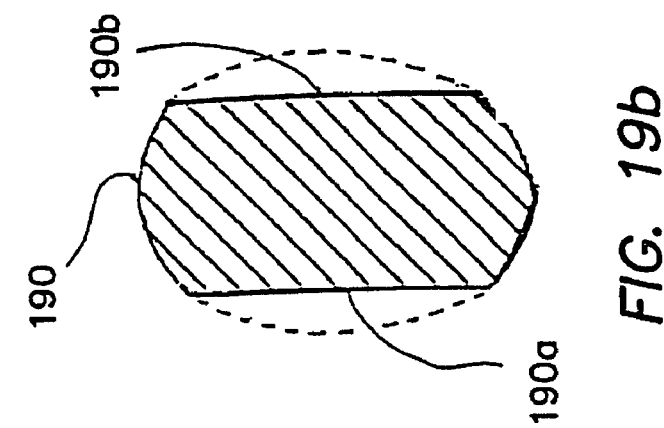
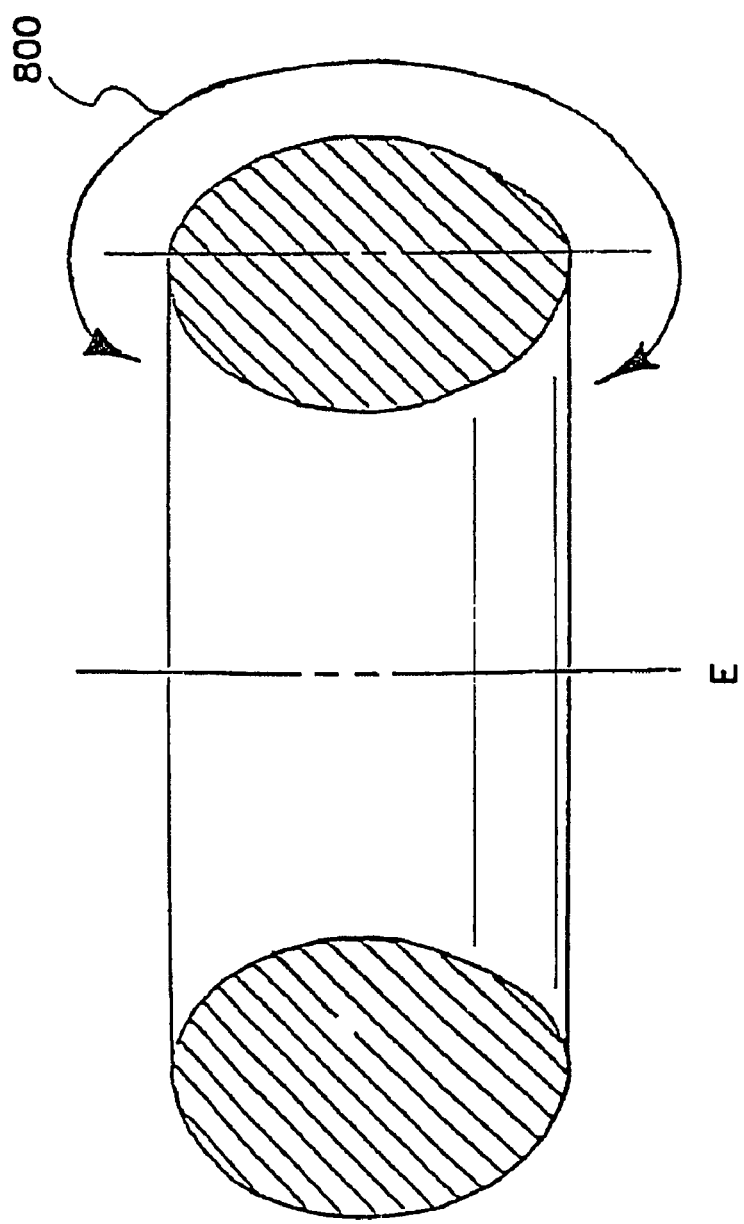

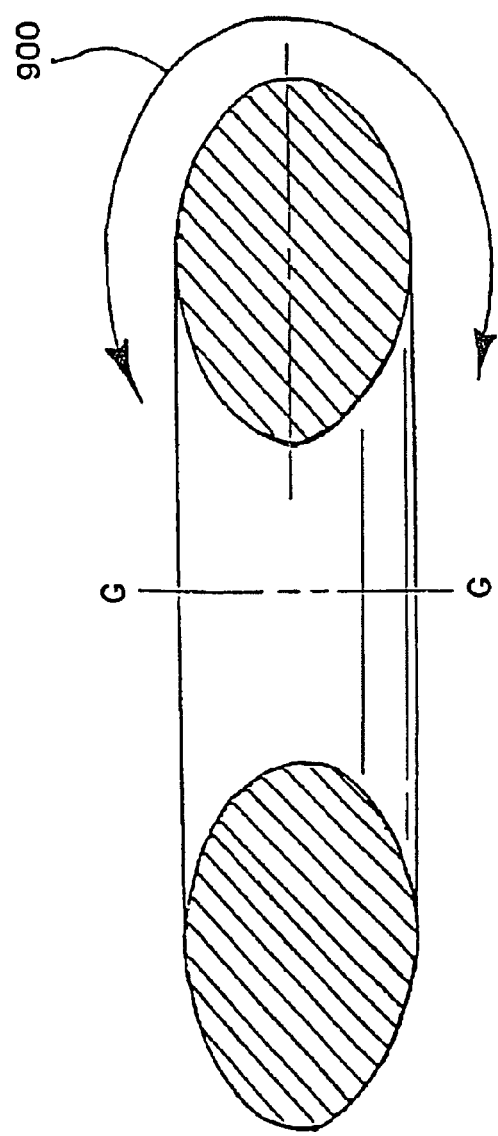
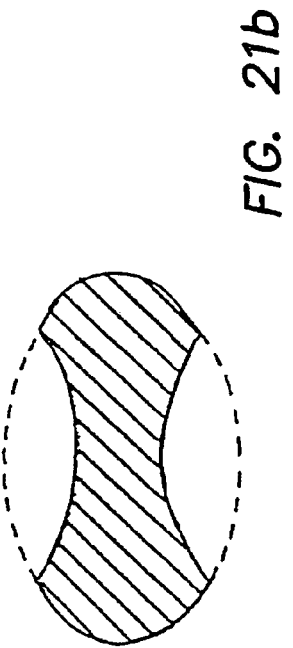
FIG. 21a
FIG. 21b

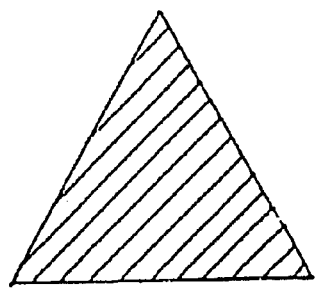
FIG. 23a
FIG. 23b
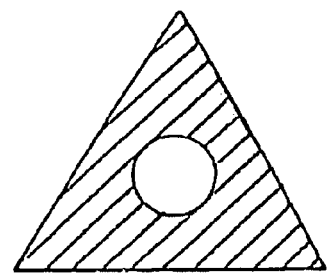
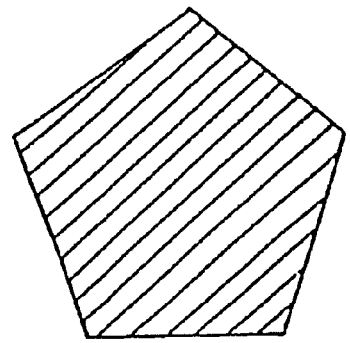
FIG. 24a
FIG. 24b
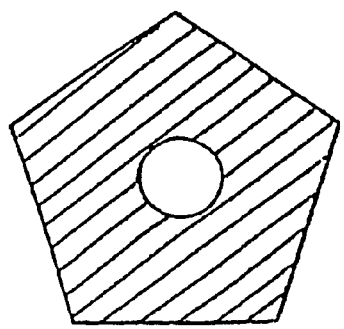

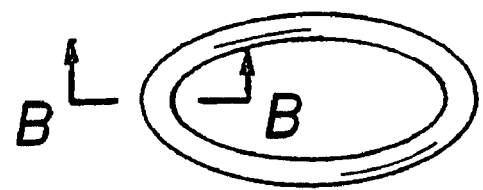
FIG. 25a
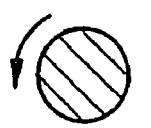
B—B
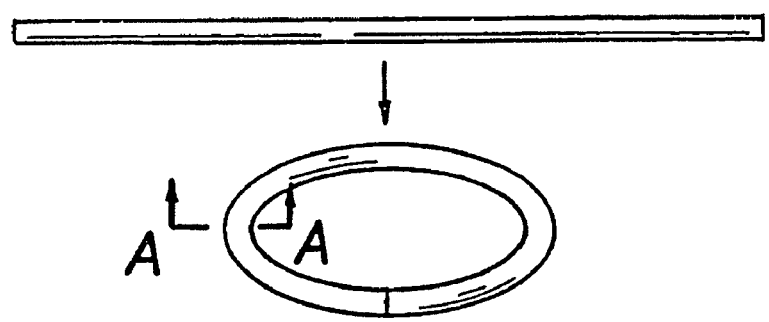
FIG. 25b
A—A

WOUND RETRACTOR

This is a 371 of PCT/US03/17389, filed Jun. 3, 2003 based on Provisional Application No. 60/386,159, filed Jun. 5, 2002, entitled "Omega Wound Retractor," and on Provisional Application No. 60/415,351, filed on Oct. 2, 2002, entitled "Wound Retractor," all of which are full incorporated herein by reference.

BACKGROUND OF THE INVENTION

1. Field of the Invention

This invention generally relates to medical devices and, more specifically, to an improved wound retractor providing ease of incremental retraction and alignment to fit a wide range of incision sizes, including audible and tactile feedback to the user.

2. Discussion of the Prior Art

Surgery typically involves making an incision large enough to accommodate a surgeon's hand and/or multiple instruments. The incision must be kept clean since it is susceptible to infection if touched by diseased body parts and/or contaminated instruments. As such, wound protectors are available to insure that exposed sides of an incision are covered and protected from contaminants. A common deficiency of wound protectors is their lack of ease of retraction adjustability and stability. U.S. Pat. Nos. 5,524,644 and 6,382,211, both to Crook, attempt to address this deficiency with a wound protector including an outer ring having an oblate cross-section and opposed flat surfaces that allegedly provide retraction adjustability and stability. The oblate design of the outer ring of Crook, however, provides only limited incremental retraction and can be difficult to twist or turn. In addition, the Crook design does not provide for an audible feedback to the user. Accordingly, there is a need in the art for an improved wound retractor that can be easily retracted to fit a wide range of incision sizes. The improved wound retractor preferably provides audible and/or tactile feedback to the user during retraction.

SUMMARY OF THE INVENTION

An incrementally adjustable wound retractor for sealing edges of a surgical incision and forming an opening in a patient's body cavity, the wound retractor comprising an inner ring, an outer ring and a flexible sleeve connecting the inner ring and the outer ring. The wound retractor provides a path for a surgeon to insert his hand and/or instruments through the opening formed by the wound retractor. The wound retractor is incrementally adjustable to fit a wide range of incision sizes. The wound retractor is installed or placed in a body cavity such that the inner and outer rings expand around inner and outer edges of the incision. Any portion of the flexible sleeve extending outside the incision can be easily rolled onto the outer ring to tightly seal the sides of the wound. The outer ring is preferably shaped to provide audible and/or tactile feedback to the user. In particular, the outer ring includes surfaces that are easy to grip and turn to allow the user to manually turn the outer ring and roll up the flexible sleeve with ease. The outer ring may be solid or include a lumen with a rod placed therein to provide audible signal to the user as the outer ring is turned.

These and other features and advantages of the invention will become more apparent with a discussion of preferred embodiments in reference to the associated drawings.

DESCRIPTION OF THE DRAWINGS

FIG. 1 illustrates a cutaway side view and an isometric view of an incrementally adjustable wound retractor in accordance with an embodiment of the invention;

FIG. 5 is a cross-section view of a hollow tube of an outer ring of a wound retractor in accordance with a second embodiment of the invention;

FIG. 6 is a cross-section view of an inner rod of the outer ring of the wound retractor in accordance with the second embodiment of the invention;

FIG. 7 illustrates a cutaway side view of an incrementally adjustable wound retractor in accordance with the second embodiment of the invention;

FIGS. 17a-17e illustrate cross-section views of additional embodiments of the outer ring of the invention;

FIGS. 18a-18l illustrate cross-section views of additional embodiments of the hollow tube and inner rod of the outer ring of the invention;

FIGS. 19a-19g illustrate cross-section views of additional embodiments of the outer ring of the invention having generally prolate cross-sections;

FIGS. 21a-21e illustrate cross-section views of additional embodiments of the outer ring of the invention having generally oblate cross-sections;

FIG. 23a illustrates a cross-section view of another embodiment of the outer ring of the invention having a triangular cross-section;

FIG. 23b illustrates a cross-section view of the outer ring of FIG. 23a further including a lumen;

FIG. 24a illustrates a cross-section view of another embodiment of the outer ring of the invention having a cross-section comprising an odd number of sides such as a pentagon;

FIG. 24b illustrates a cross-section view of the outer ring of FIG. 24a further including a lumen;

FIGS. 25a-25b illustrate different processes of forming the outer ring of the invention;

DESCRIPTION OF PREFERRED EMBODIMENTS AND BEST MODE OF THE INVENTION

Figure 2A:
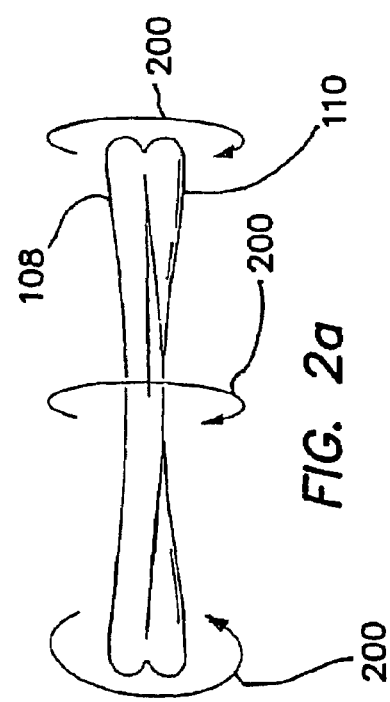
FIGS. 2a-2d illustrate the retraction of the outer ring of the wound retractor of FIG. 1 to fit a desired incision.

FIG. 1 illustrates a wound retractor 100 in accordance with a first embodiment of the invention. The wound retractor 100 comprises a first, inner ring 104, a second, double-tube outer ring 102, and a distensible sleeve 106 connecting the outer ring 102 and the inner ring 104. The sleeve 106 may be attached to the outer ring 102 and the inner ring 104 by heat seal or adhesive. The outer ring 102 and the inner ring 104 are preferably made of a material of sufficient hardness to retain their shape after twisting and rolling of the rings. That is, the material must be compliant enough to allow the outer ring 102 to be turned around its annular axis as further described below and illustrated in FIGS. 2a-2d. The shape of the outer ring 102 affects both its ability to grip and to provide stability during and after adjustment. The sleeve 106 is preferably made of a material that is flexible and impermeable to fluids and bacteria. The double-tube outer ring 102 preferably comprises a first circular tube 108 and a second circular tube 110 joined together by a small web 112. Each of the circular tubes 108 and 110 may be solid or include a lumen.

Figure 2B:
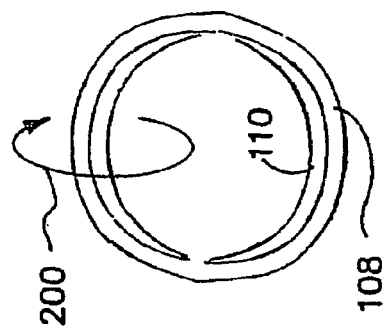
Figure 2C:
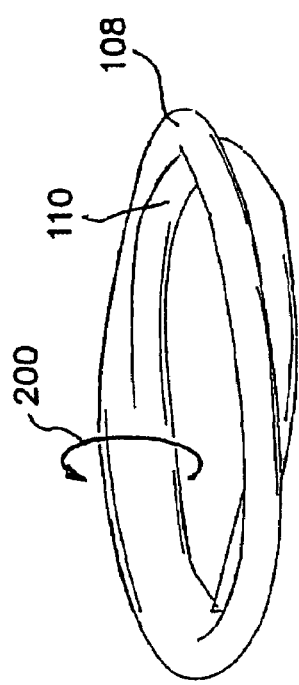

FIGS. 2a-2d illustrate the retraction and adjustment of the outer ring 102 to fit an incision. In accordance with the invention, the wound retractor 100 is axially adjustable in increments. In particular, the upper end of the sleeve 106 can be wrapped around the outer ring 102 so as to tightly seal the sides or edges of the incision. The unique shape of the outer ring 102 provides for an easy snap action when rolled about itself. The outer ring 102 also provides for incremental shortening of the sleeve 106 and for stability after installation. FIG. 3 illustrates a longitudinal cross-section view of the wound retractor 100 taken along line A-A.

Figure 4:
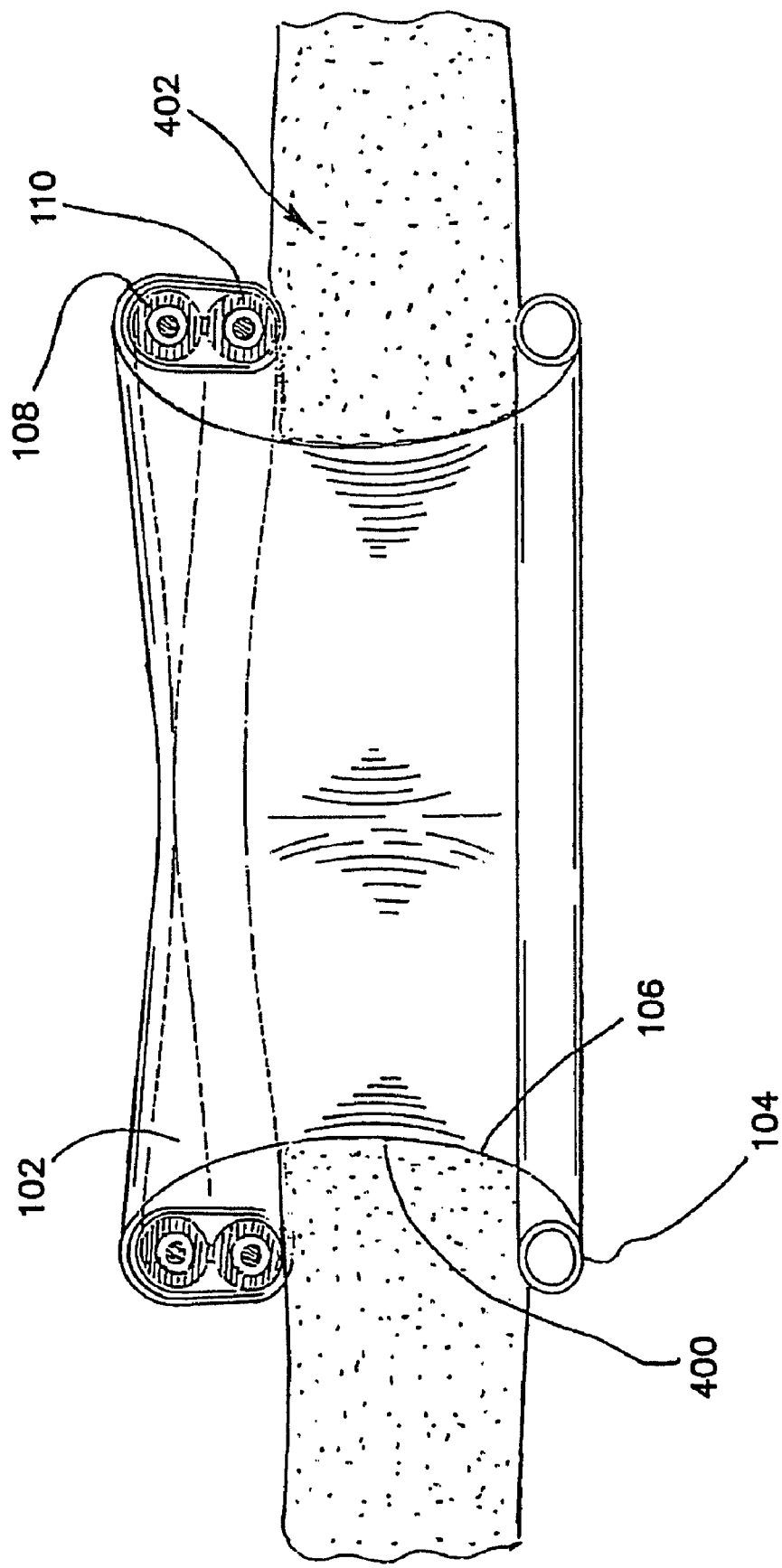
FIG. 4 illustrates the wound retractor of FIG. 1 installed in an incision.

FIG. 4 illustrates a process of installing the wound retractor 100 in a wound opening 400. An incision in the shape of a slit is first made in a patient's body, e.g., the abdominal wall. The inner ring 104 and the sleeve 106 are then manually inserted into body cavity 402 through the incision with the outer ring 102 remaining external to the body cavity 402. Once the inner ring 104 is within the body cavity 402, it expands around the inner surface of the incision so as to be generally parallel to the abdominal wall. The sleeve 106 provides a channel from the outside to the inside of the body cavity 402. The outer ring 102 initially rests above the abdominal wall around the wound opening 400. Since the upper end of the sleeve 106 is connected to the outer ring 102, the sleeve 106 can be drawn upwards and radially outward or inward, thereby drawing the inner ring 104 tightly against the inner surface of the abdominal wall. Moreover, the intermediate portion of the sleeve 106 is drawn tightly against the sides and edges of the wound opening 400, thereby retracting the adjacent tissue and producing a tightly sealed opening in the body cavity 402. That is, the sleeve 106 contacts the entire wound surface and protectively covers the same and seals it from contamination and infection. Depending on the size and depth of the incision, the user can roll up the sleeve 106 by gripping the double-tube outer ring 102 and turning it in a direction 200 as illustrated in FIGS. 2a-2c until the sleeve 106 abuts the outer edge of the wound opening 400. It should be appreciated that the outer ring 102 can be turned around its annular axis in either an outward or inward direction to roll the sleeve 106.

Figure 2D:
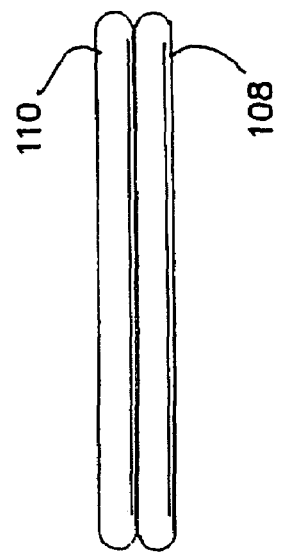
Figure 3:
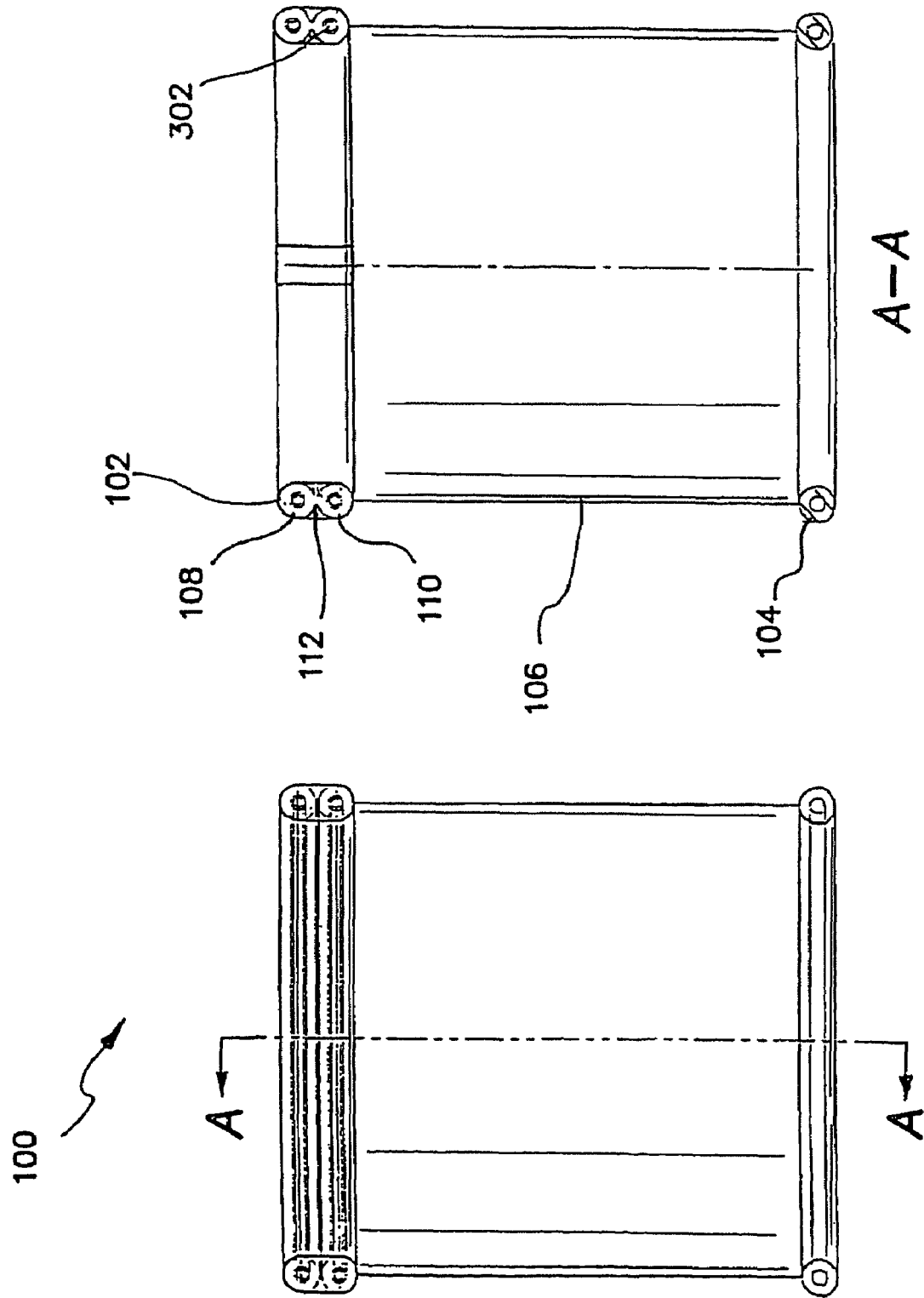
FIG. 3 is a longitudinal cross-section view of the wound retractor of FIG. 1 taken along line A-A.

The outer ring 102 has a unique and novel double-tube configuration wherein through simple manipulation of forcing a first tube in a first direction and a second tube in a second direction, the positions of the first and second tubes can be inverted resulting in fast and easy turning of the tubes as illustrated in FIGS. 2a-2d. In one embodiment of the invention, the outer ring 102 is rotated by pushing the bottom tube or second circular tube 110 inward while pulling the top tube or first circular tube 108 outward (see FIG. 2a). The combination of the above steps results in inversion of the first and second circular tubes as illustrated in FIG. 2d. That is, the outer ring 102 can be rotated in 180° turns thereby retracting the sleeve 106. The above process can be repeated until a desired compression or wound opening is achieved.

An advantage of the invention is it provides for an easier, faster and higher retraction rate than that known in the prior art, thereby resulting in less traumatic effects to the patient. Another advantage of the invention is it provides tactile gripping and incremental rolling of the sleeve about the outer ring. In the above description, the first and second tubes of the outer ring are in a vertical position but it should be appreciated that the first and second tubes may be in different positions relative to one another such as a horizontal position.

In another embodiment of the invention, a small wire 302 such as a stainless steel wire is placed inside a lumen of the double-tube outer ring 102 (see FIGS. 3 and 10-13) so as to provide an audible signal as the outer ring 102 is turned. That is, as the double-tube outer ring 102 is turned, the wire 302 deflects against the tubing wall so as to provide an audible sound feedback to the user. Another feature of the wire 302 is it provides retraction stability to the wound retractor 100.

After surgery, the wound retractor 100 may be retrieved by grabbing the inner ring 104 and the sleeve 106 and pulling them through the wound opening 400. The use of the sleeve 106 and the ease of retracting the outer ring 102 provide higher compression between the inner and outer rings. As a result, the wound retractor 100 of the invention provides incremental adjustability to fit a wide range of incision sizes and isolates and protects the wound from bacterial infection as the diseased body parts and contaminated instruments are passed through the wound.

FIGS. 5-9 and 14-16 illustrate a wound retractor 500 having a roller design in accordance with another embodiment of the invention. The wound retractor 500 comprises a first, inner ring 504, a second, outer ring 502, and a distensible sleeve 506 connecting the outer ring 502 and the inner ring 504. The sleeve 506 can be attached to the outer ring 502 and the inner ring 504 by heat seal or adhesive. The outer ring 502 includes a hollow tube or lumen 508 that has a fan-like shape cross-section as illustrated in FIG. 5. The outer ring 502 further comprises an inner rod 510 that has a similar fan-like geometry on its outer surface as illustrated in FIG. 6. The hollow tube 508 and the inner rod 510 are coaxially joined to form the outer ring 502 of the wound retractor 500.

Figure 8:
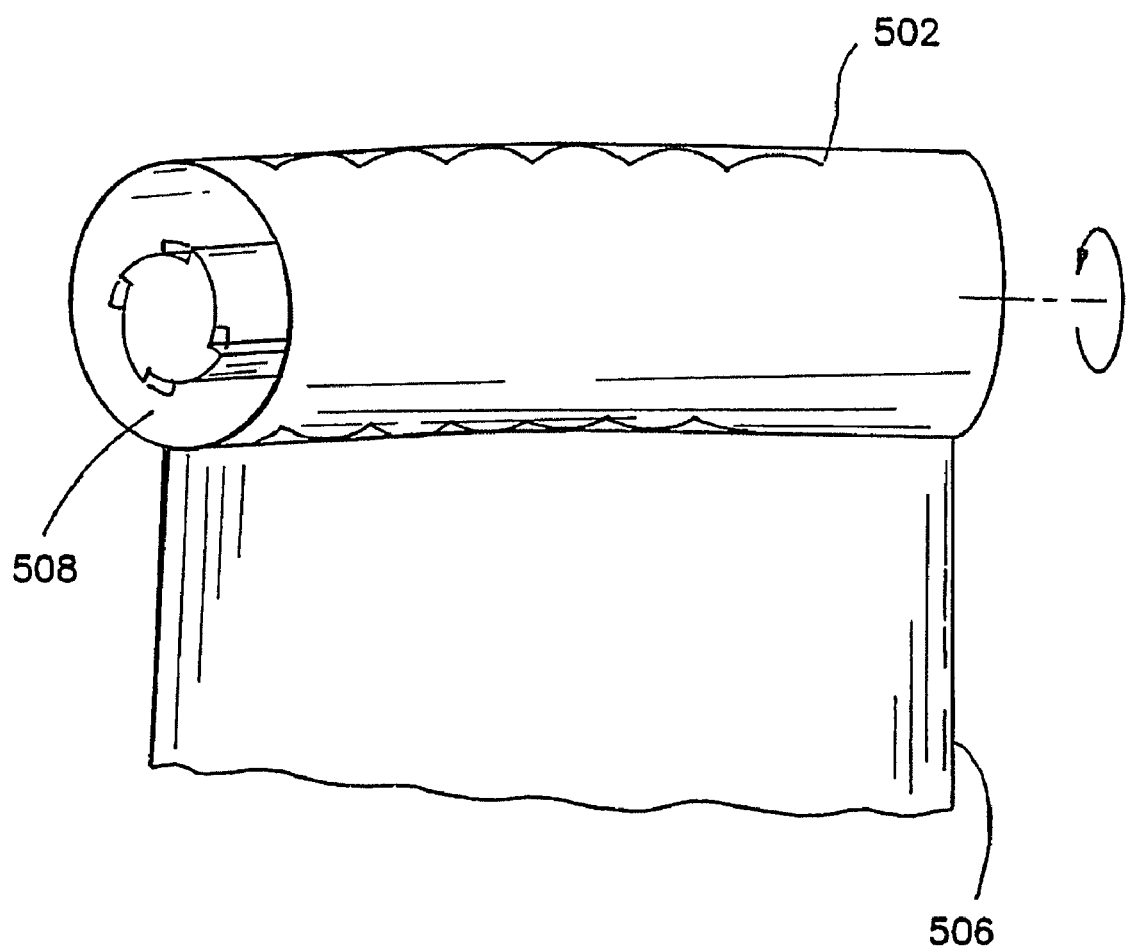
FIG. 8 illustrates the retraction and alignment of the outer ring to fit a desired incision size in accordance with the second embodiment of the invention.

The fan-like geometry of the outer ring 502 serves as an incremental rotating mechanism. In particular, when the hollow tube 508 is manually rolled out of its coaxial alignment with respect to the inner rod 510, the hollow tube 508 will index itself until it matches the next alignment point of the inner rod 510 as illustrated in FIG. 8. When the hollow tube 508 and the inner rod 510 are coaxially aligned, they lock in place preventing further indexing until the steps of retracting are repeated. It is appreciated that each of the hollow tube 508 and the inner rod 510 has at least one alignment point providing indexing and incremental rotation of the outer ring 502. That is, the outer ring 502 can incrementally retract in steps based on the number of alignment points or indexes on the fan.

Figure 9:
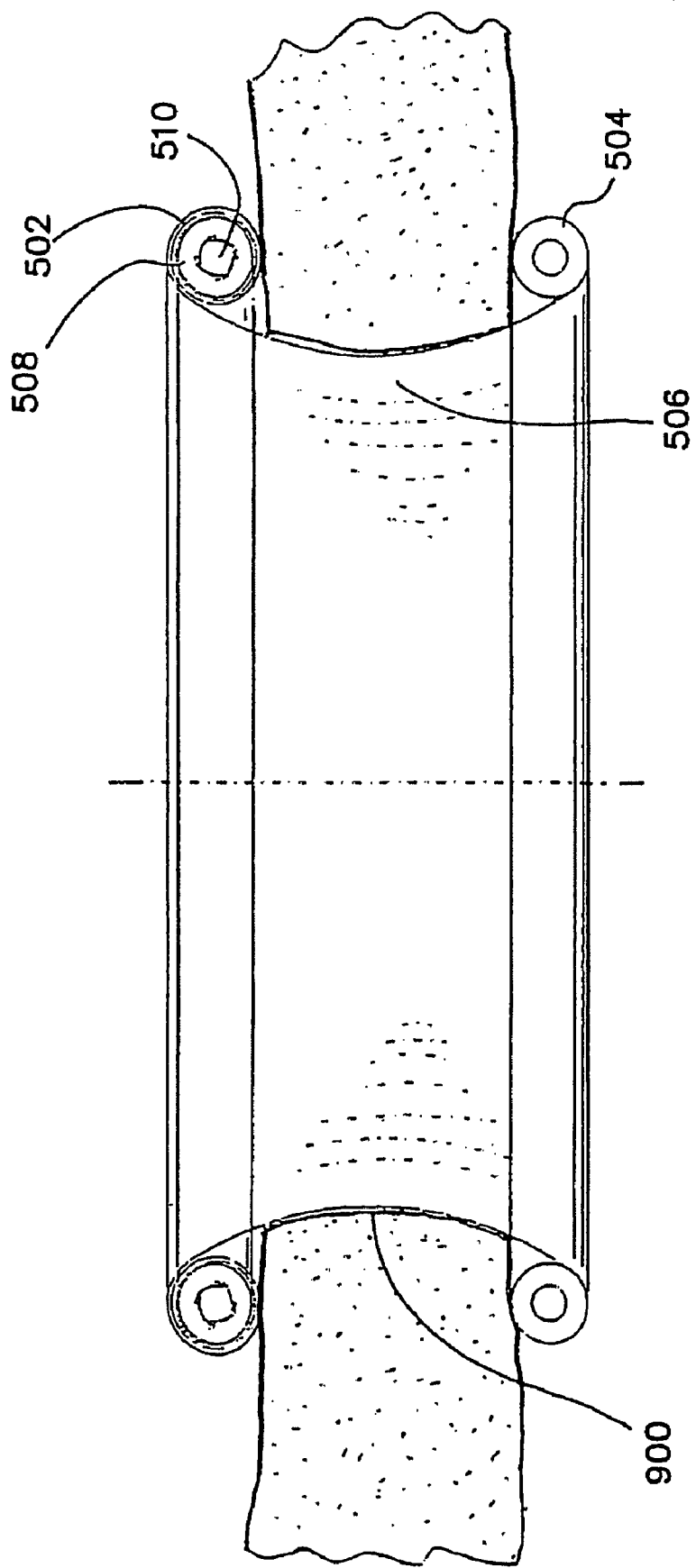
FIG. 9 illustrates the wound retractor of FIG. 7 installed in an incision.
Figure 10:
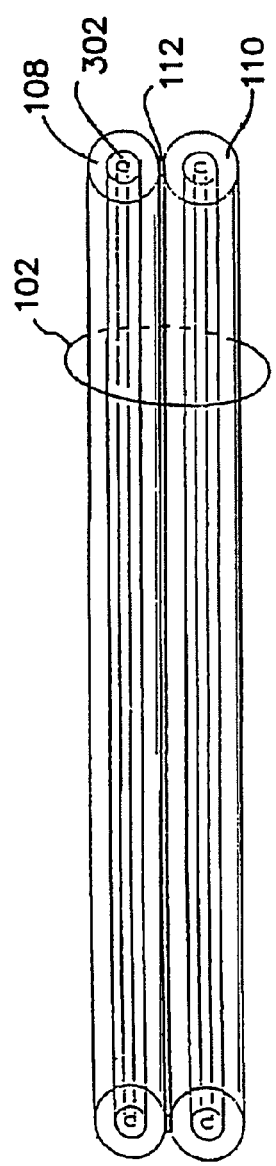
FIG. 10 illustrates a longitudinal cross-section view of an outer ring including a wire in accordance with a third embodiment of the invention.
Figure 11:
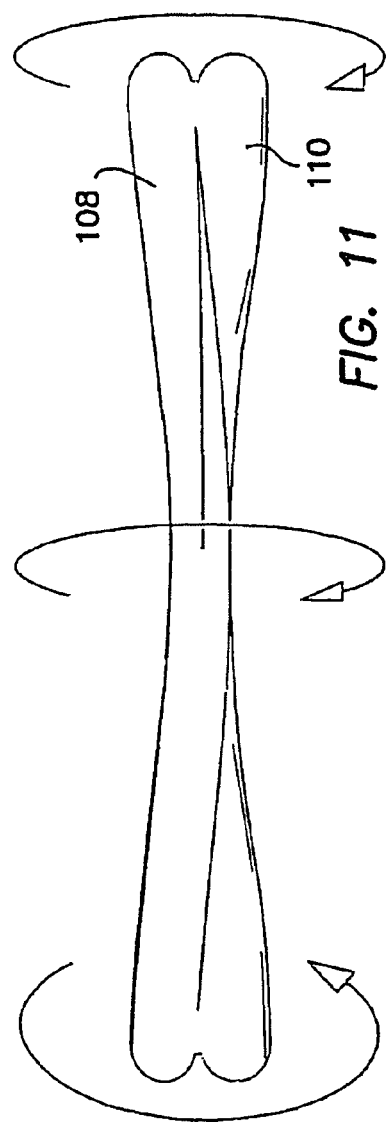
FIGS. 11 and 12 illustrate the rolling of the outer ring to fit a desired incision size in accordance with the third embodiment of the invention.
Figure 12:
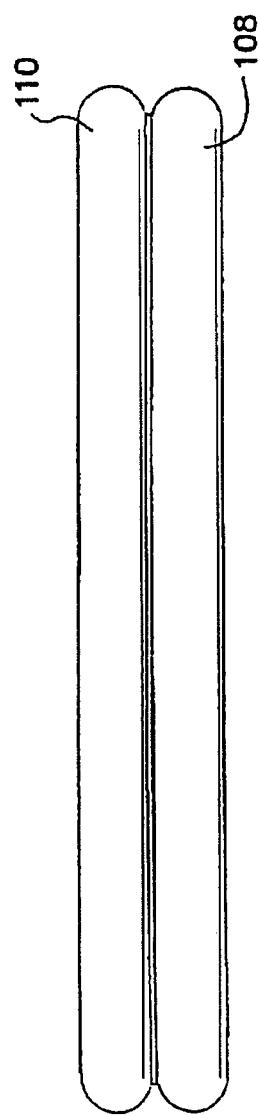
Figure 13:
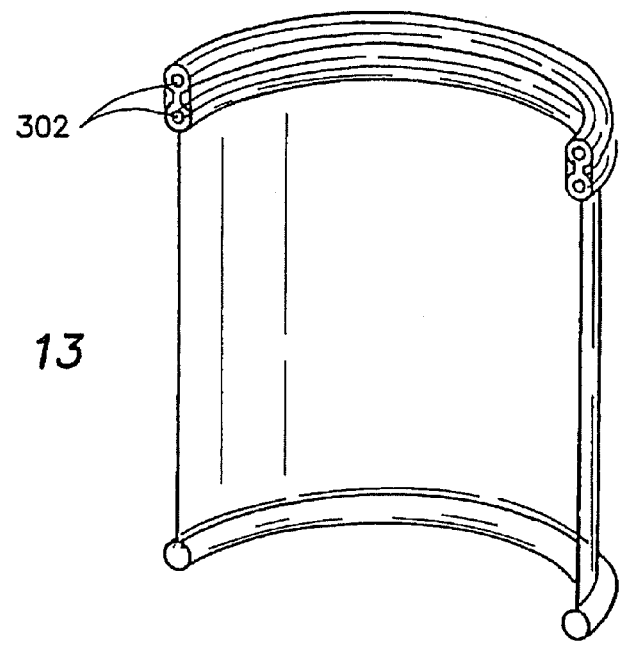
FIG. 13 is a three-dimensional cross-section view of the wound retractor of FIG. 10.
Figure 14:
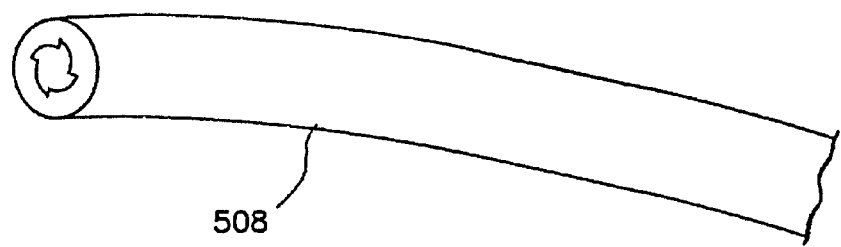
FIG. 14 is a three-dimensional image of the hollow tube of the outer ring of the wound retractor in accordance with the second embodiment of the invention.
Figure 15:
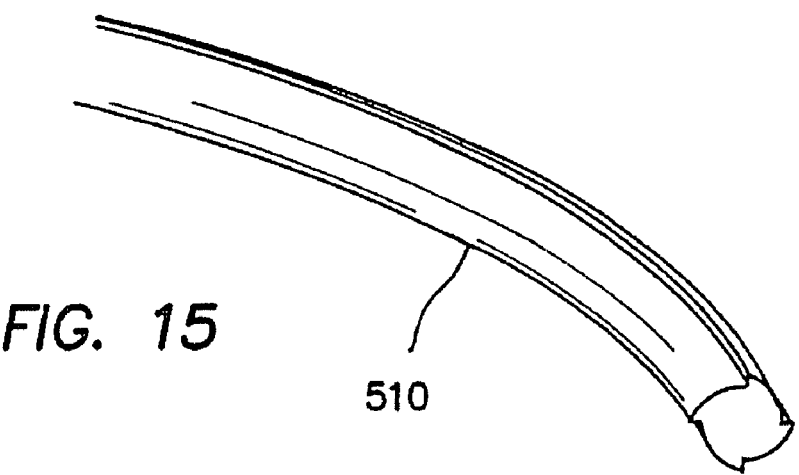
FIG. 15 is a three-dimensional image of the inner rod of the outer ring of the wound retractor in accordance with the second embodiment of the invention.
Figure 16:
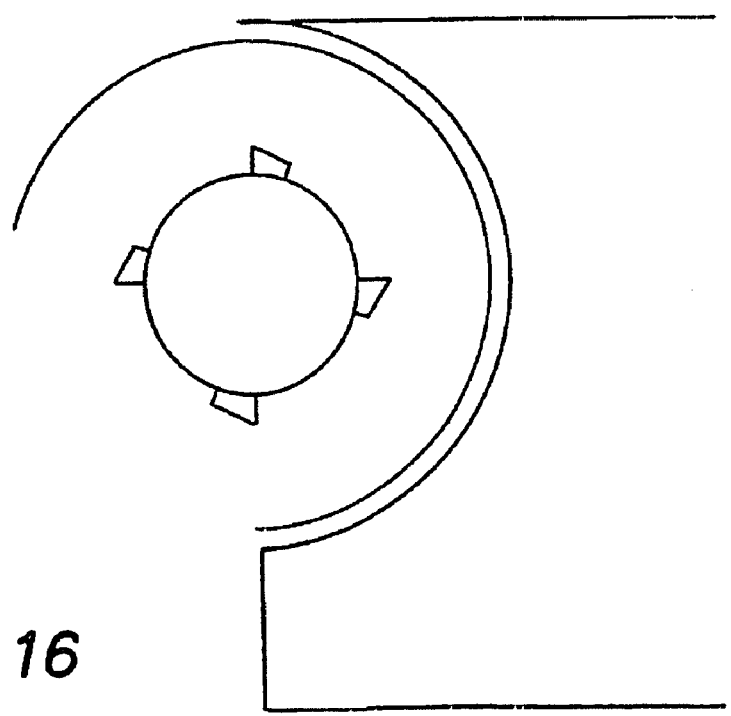
FIG. 16 is a cross-section view of the hollow tube and inner rod coaxially joined in accordance with the second embodiment of the invention.
Figure 17B:
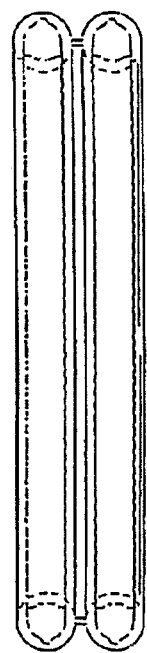
Figure 17C:
Figure 17A:
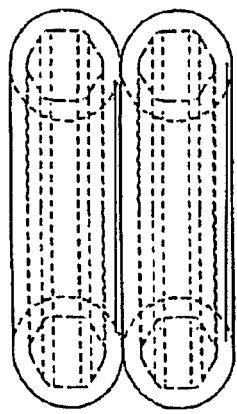

FIG. 9 illustrates a process of installing the wound retractor 500 in a wound opening 900. An incision in the shape of a slit is first made in a patient's body, e.g., the abdominal wall. The inner ring 504 and the sleeve 506 are then manually inserted and positioned underneath and along the edges of body cavity wall 512, and the outer ring 502 is pulled through the wound opening 900 so as to be placed outside the body cavity wall 512. Retraction of the sleeve 506 can then be achieved by rolling the outer ring 502 over the sleeve 506 in a direction 700 as shown in FIG. 7 until a desired compression or wound opening is achieved. Incremental retraction is achieved by manually rolling the hollow tube 508 out of its coaxial alignment with the inner rod 510, i.e., the hollow tube 508 can be rolled and indexed to match the next alignment point between the hollow tube 508 and the inner rod 510.

When the hollow tube 508 and the inner rod 510 are coaxially aligned, they lock in place preventing further indexing until the outer ring 502 is rolled out of its alignment again. This process is repeated until a desired retraction is achieved. Once surgery is complete, the wound retractor 500 can be retrieved by grabbing the inner ring 504 and the sleeve 506 and pulling them through the wound opening 900.

It is appreciated that the second, outer ring can be designed in various shapes and sizes to achieve various retraction rates and/or to conform with different body surfaces as illustrated in FIGS. 17a-17e. For example, the outer ring may comprise a single or multiple tubes of different shapes and sizes. The single or multiple tubes may be solid or include lumens of different shapes and sizes.

Similarly, the wound retractor having the roller design could be of various geometries. As illustrated in FIGS. 18a-18l, hollow tubes 508a-508l and inner rods 510a-510l, respectively, of the second, outer ring may have different shapes and sizes and may contain multiple locking mechanisms. For example, the inner rods 510b-510e and 510l have solid rectangular cross-sections. In comparison, the inner rods 510f-510k have hollow circular cross-sections. The hollow tubes and inner rods may be made of the same or different materials (e.g., soft and/or hard). For example, the inner rods may be rigid such as a wire or piece of metal, or they may be flexible such as an extension spring. The lumens of the hollow tubes 508a-508l may have cross-sections of different geometries such as fan-like geometry, circular, oval, circular with lumps, triangular, rectangular, any geometric shape with multiple sides, etc. Advantages of the above embodiments of the invention include improved retraction adjustability and stability.

Figure 19E:
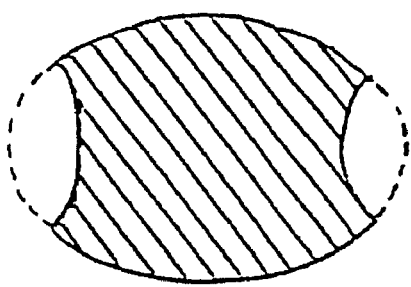
Figure 19D:
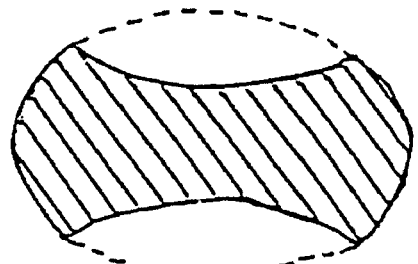
Figure 19C:
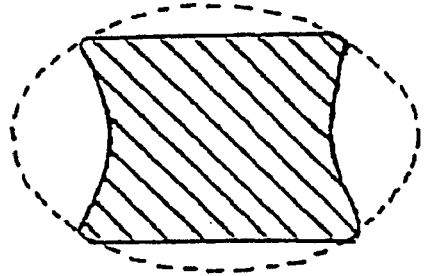
Figure 19G:
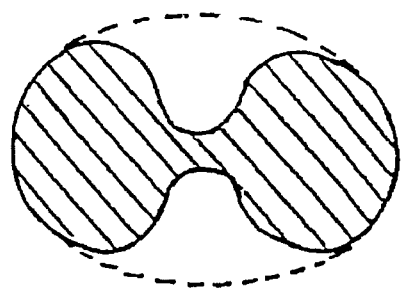
Figure 19F:
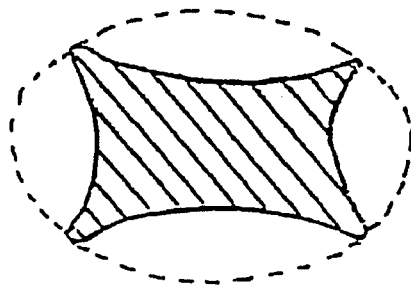
Figure 20B:
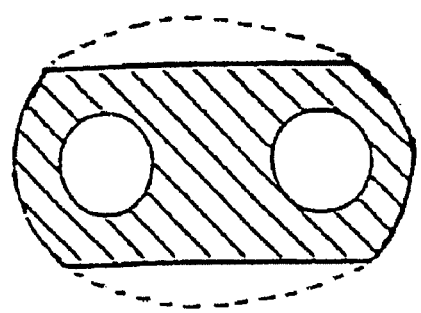
FIGS. 20a-20g illustrate cross-section views of additional embodiments of the outer ring of the invention having generally prolate cross-sections and including lumens.
Figure 20A:
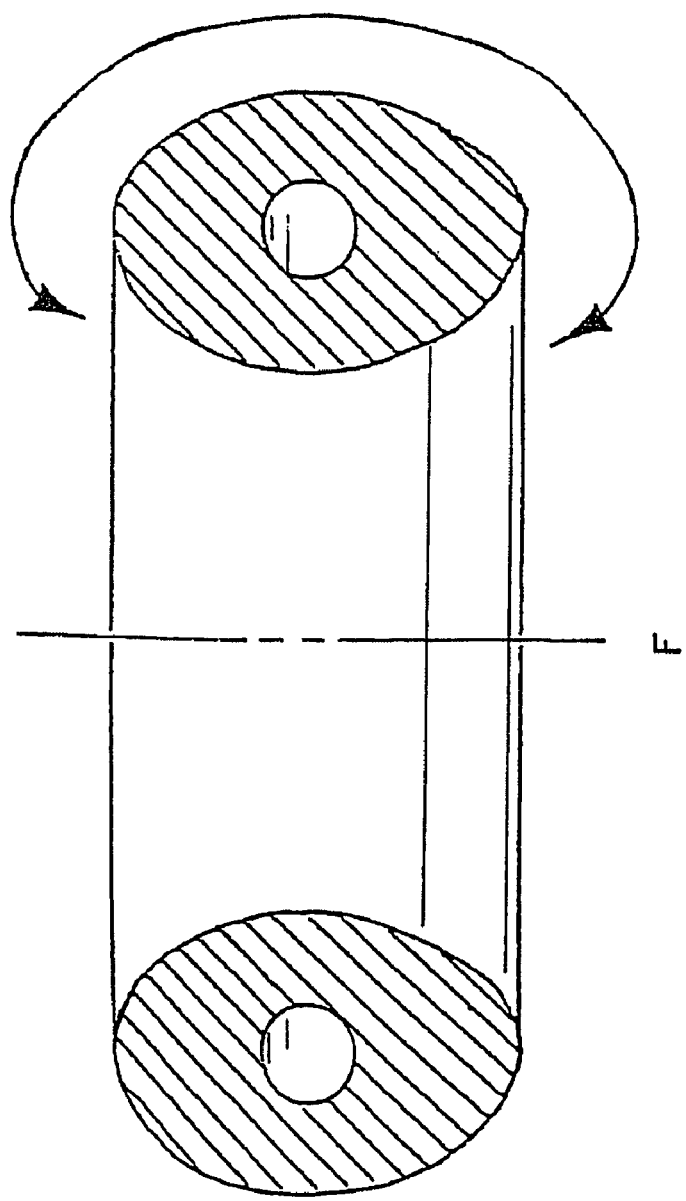
Figure 20C:
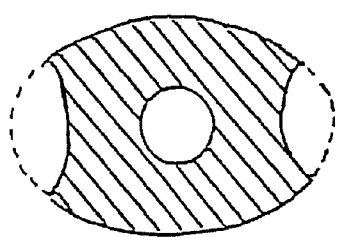
Figure 20D:
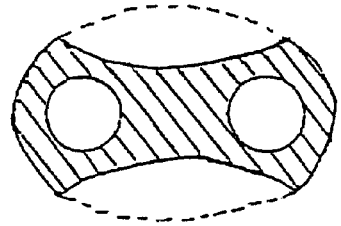
Figure 20E:
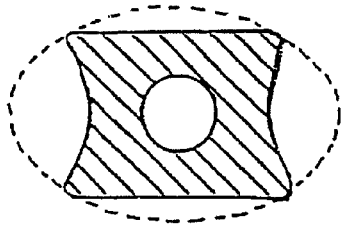
Figure 20F:
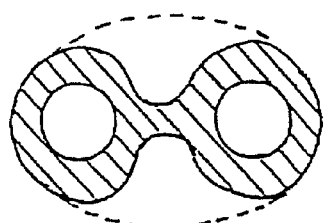
Figure 20G:
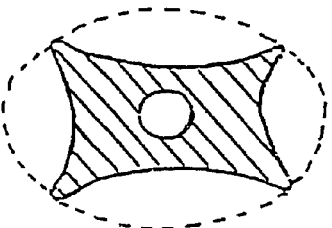

FIGS. 19a-19g illustrate cross-section views of additional embodiments of the second, outer ring of the invention having generally prolate cross-sections. That is, the longer axis of the cross-section of the outer ring is generally parallel to axis E-E as illustrated in FIG. 19a. The outer ring can be turned around the axis E-E in either an outward or inward direction 800 to roll up the sleeve (not shown). The outer rings of FIGS. 19a-19g provide tactile gripping and incremental rolling of the sleeve about the rings. FIG. 19b illustrates an outer ring 190 having two straight chordal surfaces 190a and 190b that are generally parallel to the axis E-E. FIG. 19c illustrates an outer ring having two straight chordal surfaces and two curved chordal surfaces. FIGS. 19d-19g illustrate outer rings having at least two curved chordal surfaces.

FIGS. 20a-20g illustrate cross-section views of the second, outer rings of FIGS. 19a-19g, respectively, further including at least one lumen in each ring. The lumen may house an inner rod (not shown) that deflects against the lumen wall providing an audible feedback to the user. The lumen and inner rod may be of different geometries and sizes.

Figure 21C:
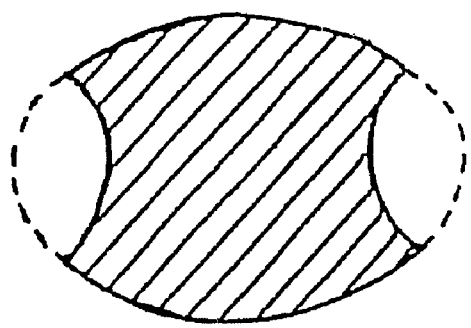
Figure 21D:
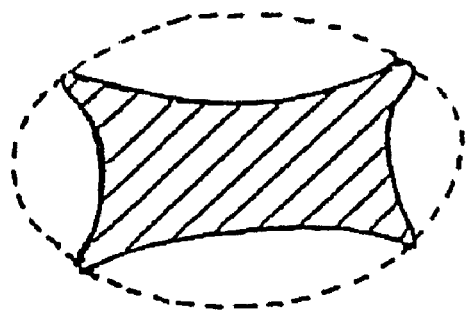
Figure 21E:
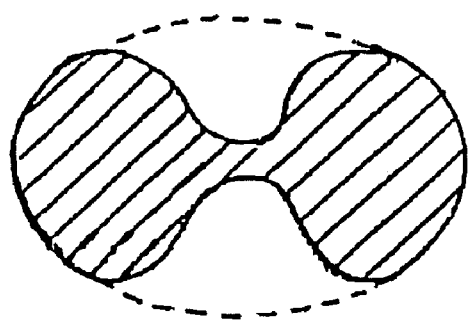
Figure 22B:
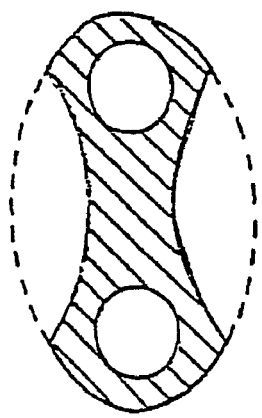
FIGS. 22a-22e illustrate cross-section views of additional embodiments of the outer ring of the invention having generally oblate cross-sections and including lumens.
Figure 22A:
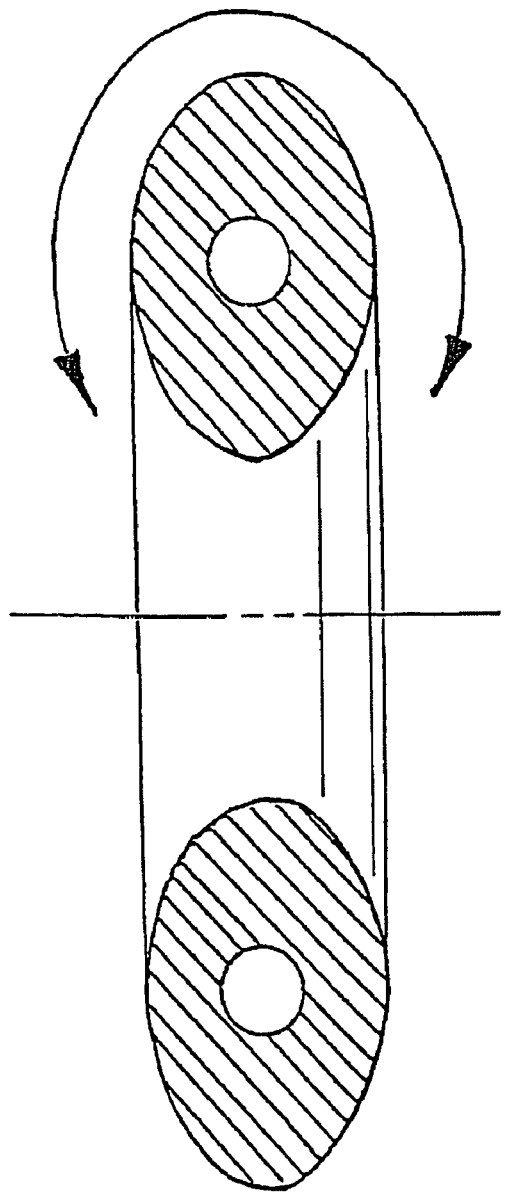
Figure 22C:
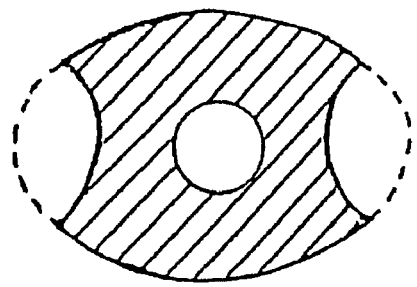
Figure 22D:
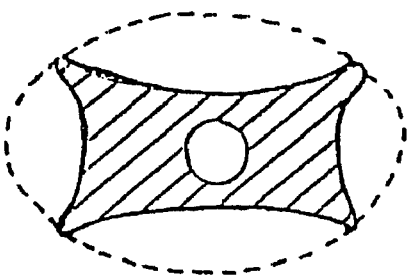
Figure 22E:
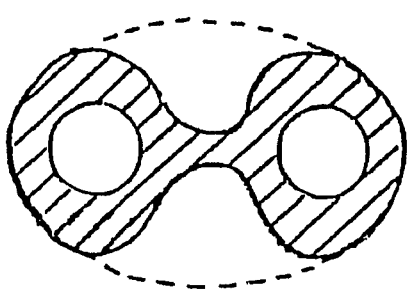

FIGS. 21a-21e illustrate cross-section views of additional embodiments of the second, outer ring of the invention having generally oblate cross-sections. That is, the longer axis of the cross-section of the outer ring is generally perpendicular to axis G-G as illustrated in FIG. 21a. The outer ring can be turned around the axis G-G in either an outward or inward direction 900 to roll up the sleeve (not shown). The outer rings of FIGS. 21a-21e provide tactile gripping and incremental rolling of the sleeve about the rings FIGS. 21b-21e illustrate outer rings having at least two curved chordal surfaces.

FIGS. 22a-22e illustrate cross-section views of the second, outer rings of FIGS. 21a-21e, respectively, further including at least one lumen in each ring. The lumen may house an inner rod (not shown) that deflects against the lumen wall providing an audible feedback to the user. The lumen and inner rod may be of different geometries and sizes.

FIG. 23a illustrates a cross-section view of another embodiment of the second, outer ring of the invention having a triangular cross-section, and FIG. 23b illustrates a cross-section view of the second, outer ring of FIG. 23a further including a lumen. In another embodiment of the invention, FIG. 24a illustrates a cross-section view of the second, outer ring of the invention having an odd number of sides such as a pentagon, and FIG. 24b illustrates a cross-section view of the second, outer ring of FIG. 24a further including a lumen. These outer rings provide tactile gripping and incremental rolling of the sleeve about the rings. The lumens of the outer rings in FIGS. 23b and 24b may be of different shapes and sizes to house inner rods (not shown) having different shapes and sizes. It is appreciated that the outer ring can be designed in various shapes and sizes to achieve various retraction rates and/or to conform with different body shapes.

FIGS. 25a-25b illustrate different processes of forming the second, outer ring of the invention. The outer ring, which may be solid or include a lumen, may be molded as a circular ring as shown in FIG. 25a, or the outer ring may be formed by joining a single or multiple extruded tubes into a circular ring as shown in FIG. 25b.

In another embodiment of the invention, access into and out of a patient's body is achieved by a hand assisted laparoscopic (HAL) procedure using a surgical access device such as the Gelport™ device as described in applicant's international application PCT/US01/29682, filed on Sep. 21, 2001, entitled "Surgical Access Apparatus and Method," which is incorporated herein by reference, while retraction is provided by the wound retractor of the present invention. The purpose of this embodiment is to combine the features and advantages of both the wound retractor of the present invention and the surgical access device as described in the PCT application. As explained in the PCT application, the current surgical access device uses a polyisoprene sheath that is wrapped distally around an O-ring, and once placed into a wound incision, the sheath is then stretched over extended tabs onto an abdominal base. The sheath of the surgical access device requires stretching and often times requires multiple attempts to secure it to the abdominal base. A novelty of this embodiment is to modify the cap and/or the abdominal base of the surgical access device so that it will accept the wound retractor of the present invention to replace the polyisoprene sheath and to maintain an airtight seal. The use of the wound retractor would simplify the HAL procedure and would not require stretching.

Figure 26:
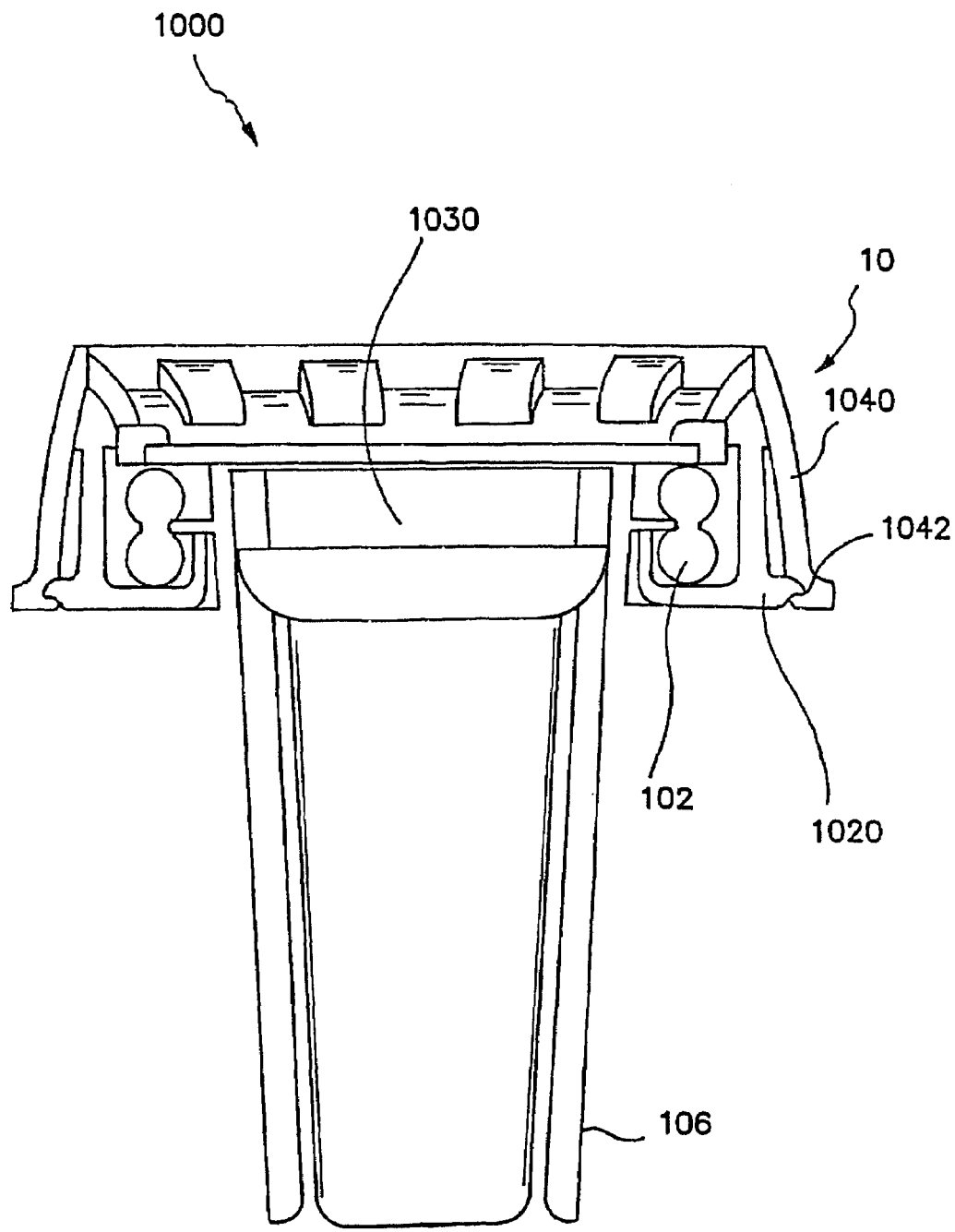
FIG. 26 illustrates an axial cross-section view of a surgical access device with a slightly modified gel cap and/or abdominal base in accordance with another embodiment of the invention.
Figure 27:
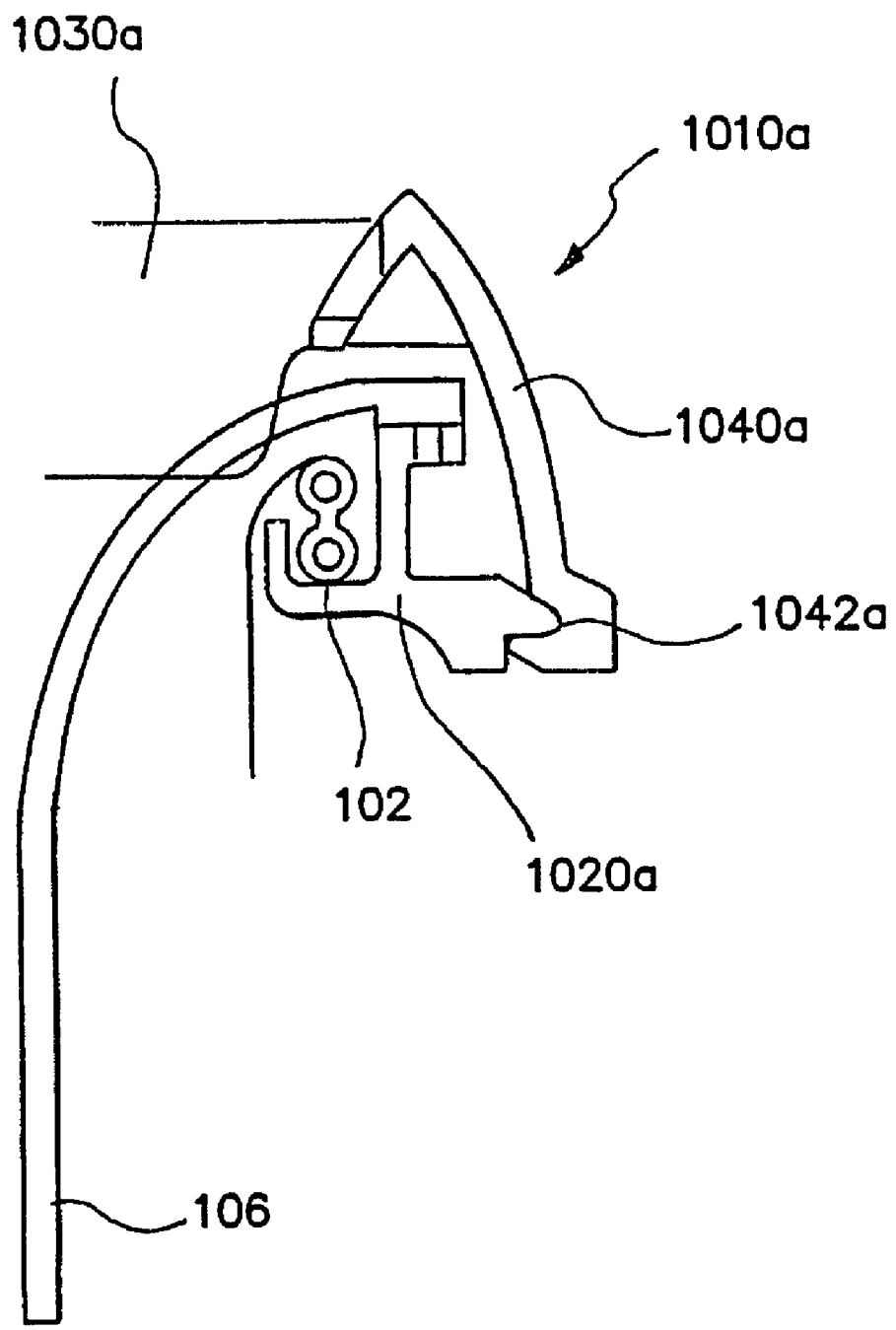
FIG. 27 is an axial cross-section view of a surgical access device in accordance with another embodiment of the invention.
Figure 28:
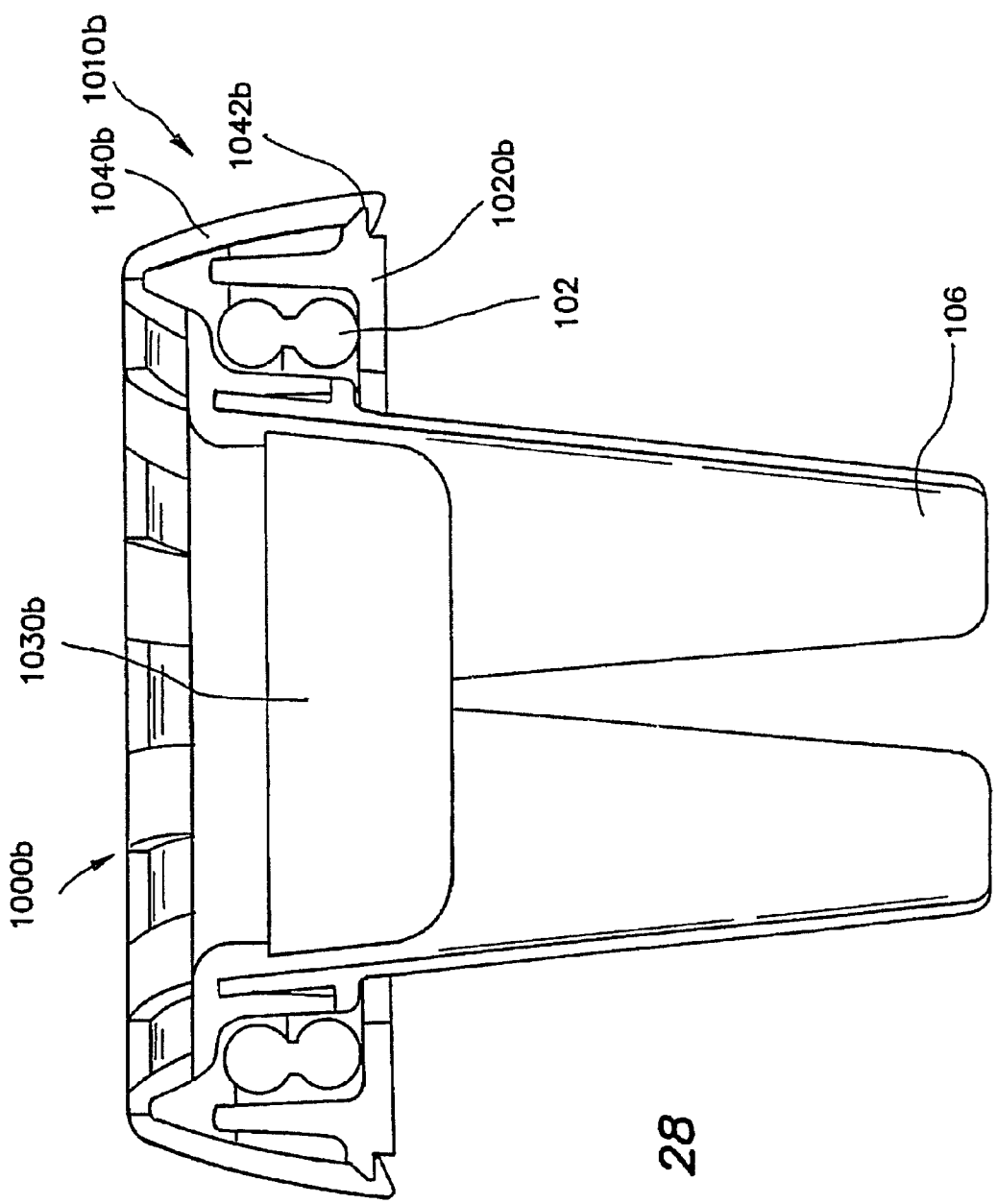
FIGS. 28-30 illustrate additional exemplary embodiments of the invention having modifications that could be made to the gel cap and/or the abdominal base so that the surgical access device can be used with the wound retractor.
Figure 29:
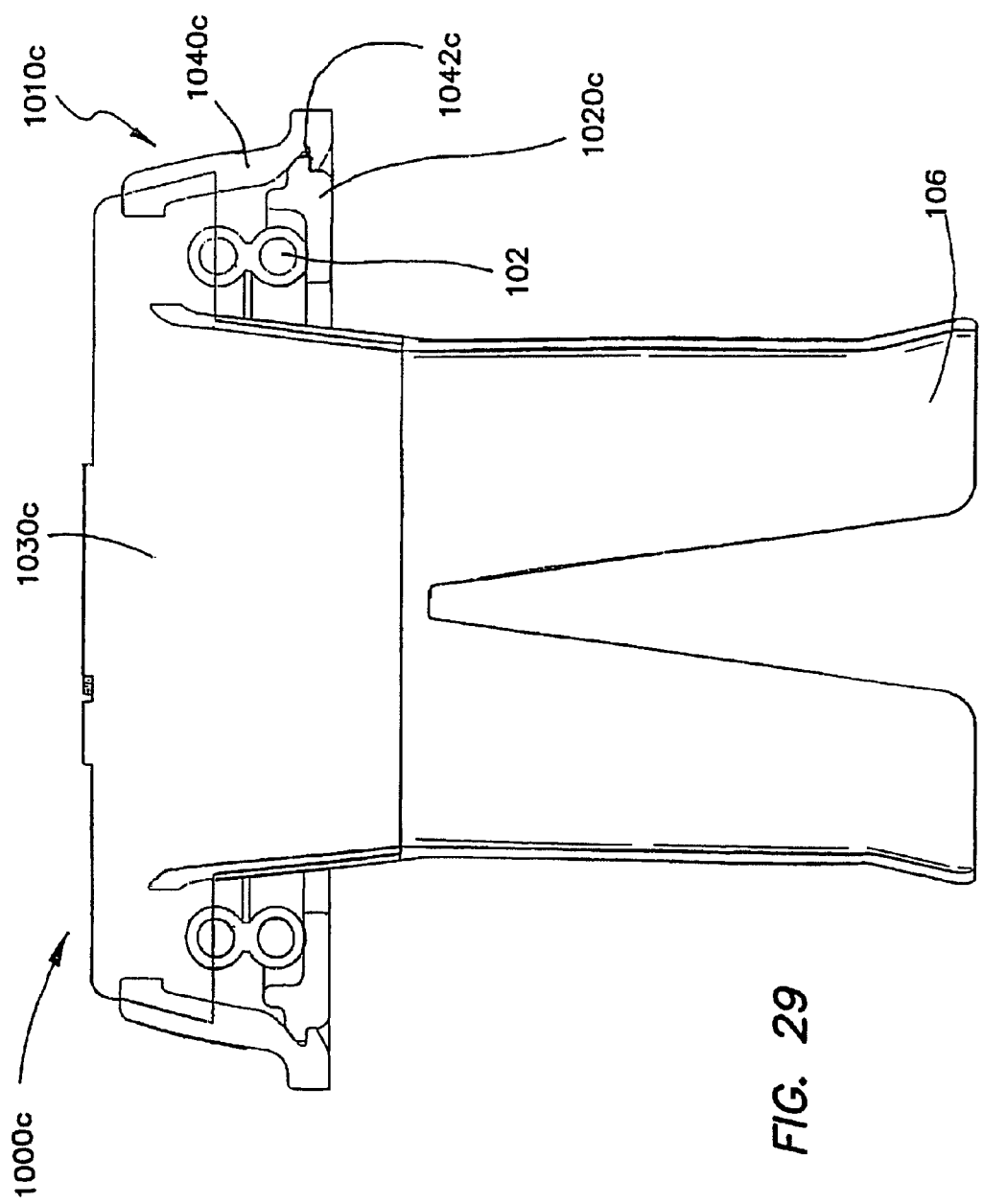
Figure 30:
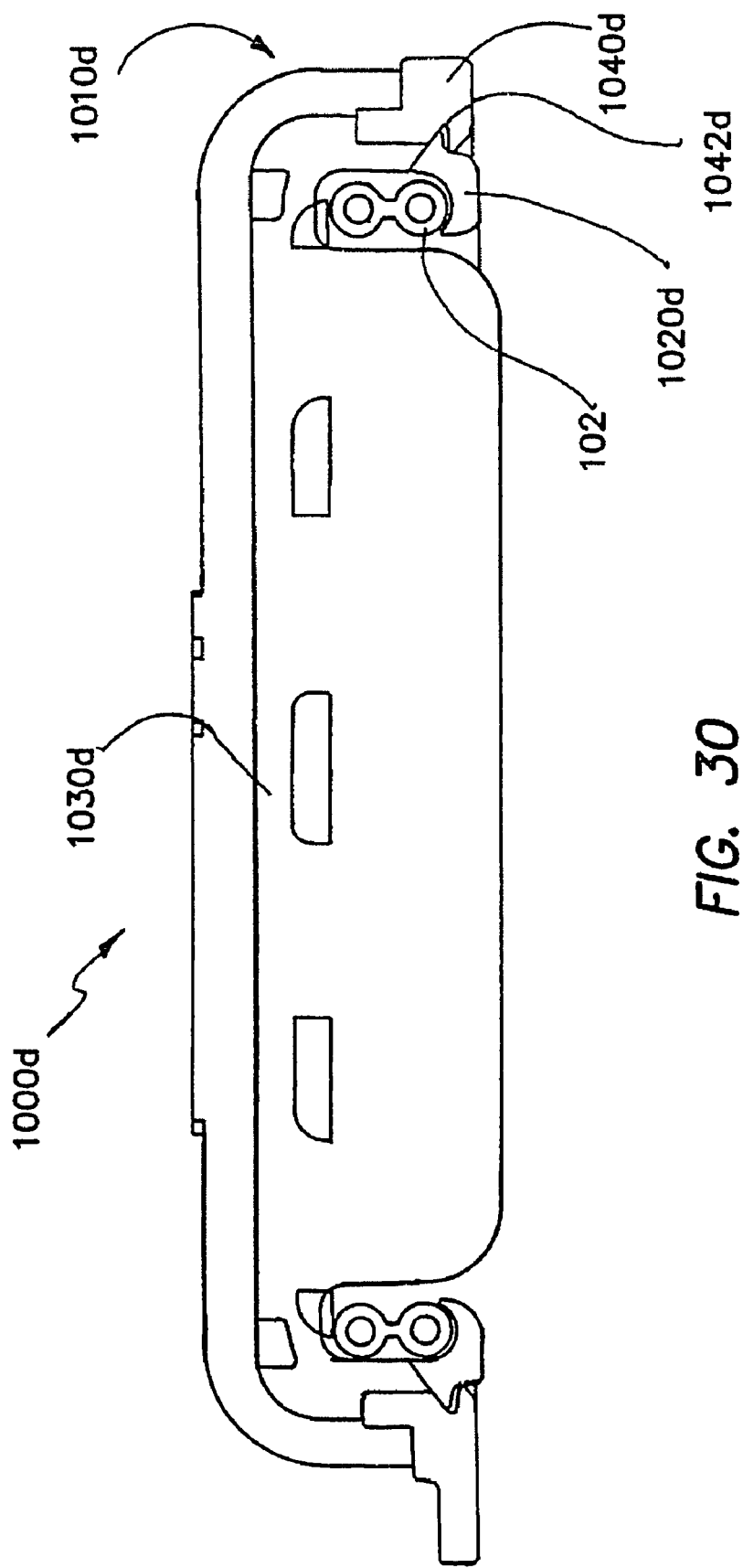

Referring to FIG. 26, there is shown a surgical access device 1000 with slight or moderate modifications to a gel cap 1010 and to an abdominal base 1020. The gel cap 1010 further includes a gel pad 1030 and a circumferential cap ring 1040, which can be inserted and molded to the pad 1030. The resulting gel cap 1010 forms a seal with the base 1020, thereby defining a working channel through the pad 1030, the cap ring 1040, the base 1020, and the sleeve 106 of the wound retractor. In this manner, the working channel includes a single valve formed by the gel pad 1030 which provides both a zero seal and an instrument seal for a wide range of instrument diameters. Referring to FIG. 27, the cross-section view of gel cap 1010a illustrates an annular void 1042a that is formed on the inner circumference of cap ring 1040a. This void is of particular advantage in forming a sealing relationship with base 1020a. FIGS. 28-30 illustrate additional exemplary embodiments of the invention having modifications that could be made to the gel cap and/or the abdominal base so that the surgical access device can be used with the wound retractor.

Figure 31:
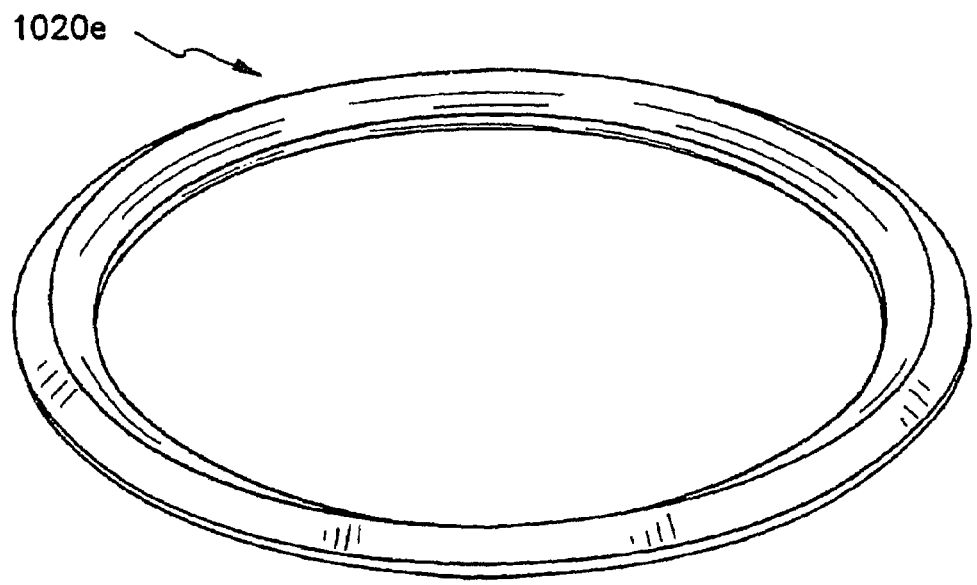
FIG. 31 illustrates a perspective view of a base of a surgical access device in accordance with another embodiment of the invention.
Figure 32:
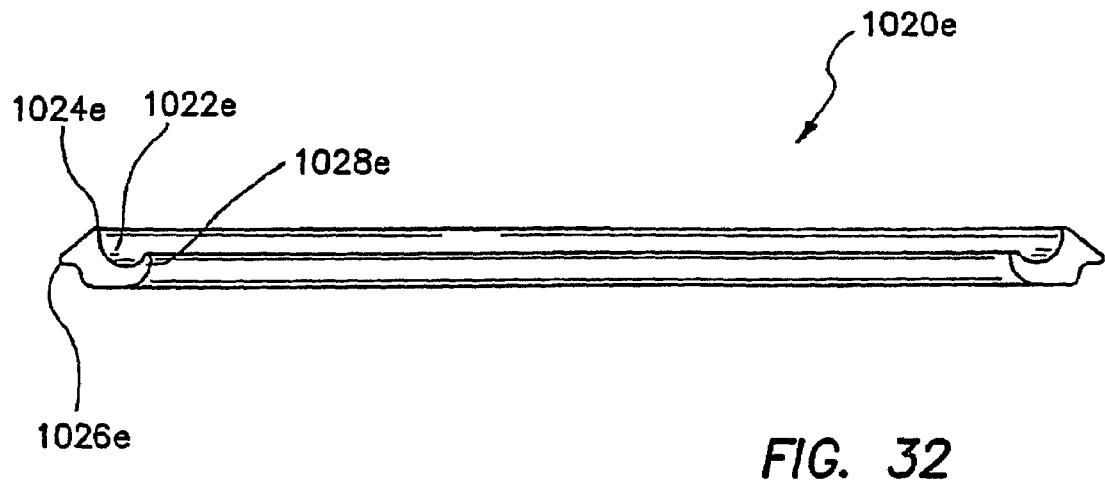
FIG. 32 is an axial cross-section view of the embodiment illustrated in FIG. 31.

FIG. 31 illustrates a perspective view of a base 1020e in accordance with another embodiment of the invention. FIG. 32 is an axial cross-section view of the embodiment illustrated in FIG. 31. From these views, it will be noted that the base 1020e can be provided with a smooth generally cylindrical inner surface 1022e which extends proximally to a rounded end surface 1024e and outwardly from the end surface 1024e along an annular lip 1026e, which is sized and configured to fit into an annular void formed on the inner circumference of a corresponding cap ring. Proximally of the inner surface 1022e, the base 1020e can also include a rounded end surface 1028e along its inner diameter for securing the second, outer ring of the wound retractor once the sleeve has been shortened.

Figure 33:
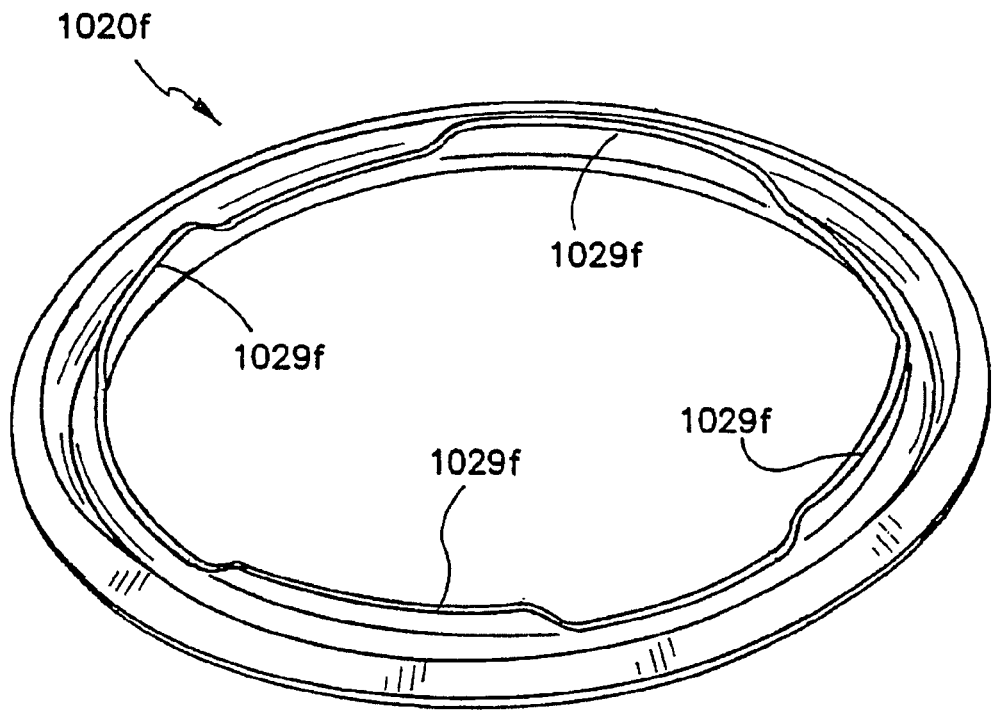
FIGS. 33 and 34 illustrate a base of a surgical access device in accordance with another embodiment of the invention having at least one toggle or latch adapted to fit a corresponding cap ring.
Figure 34:
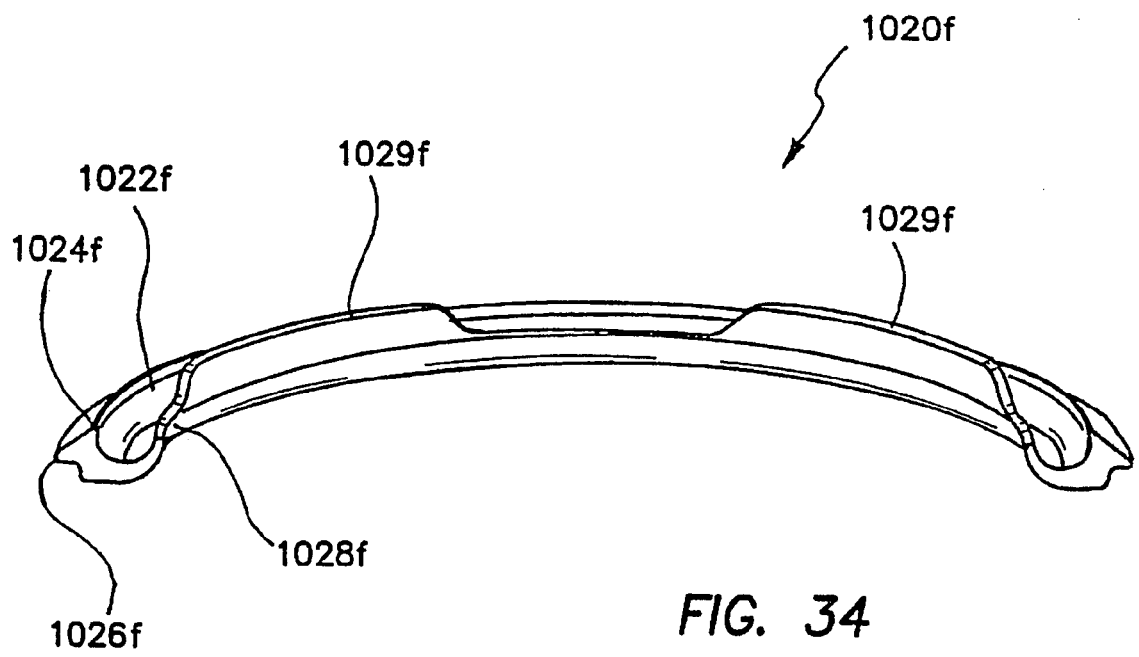
Figure 35:
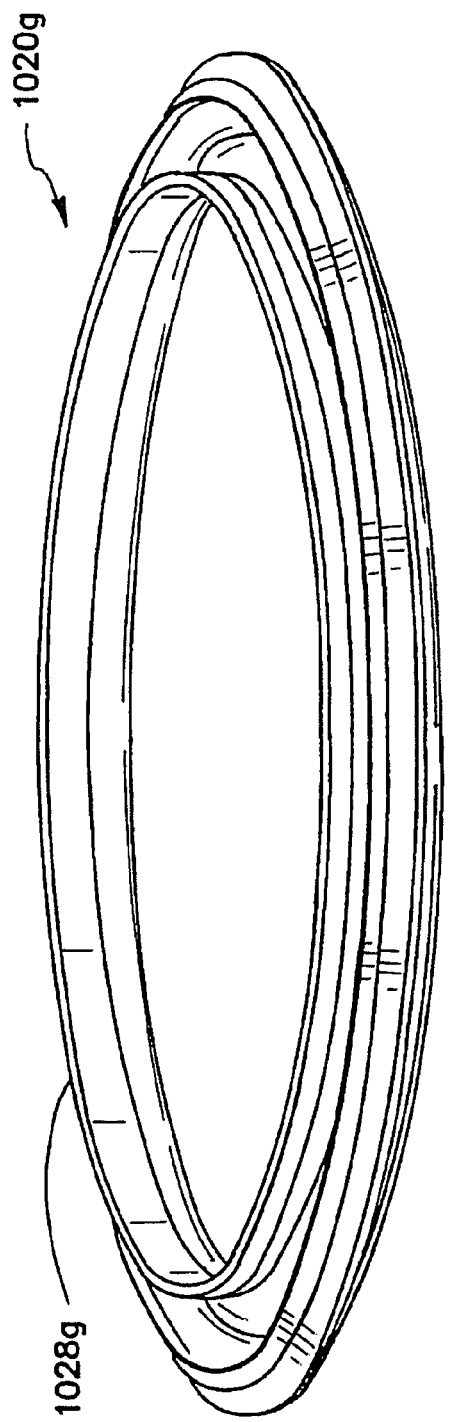
FIGS. 35 and 36 illustrate a base of a surgical access device in accordance with another embodiment of the invention having a raised wall on an inner diameter and adapted to fit a corresponding cap ring.
Figure 36:
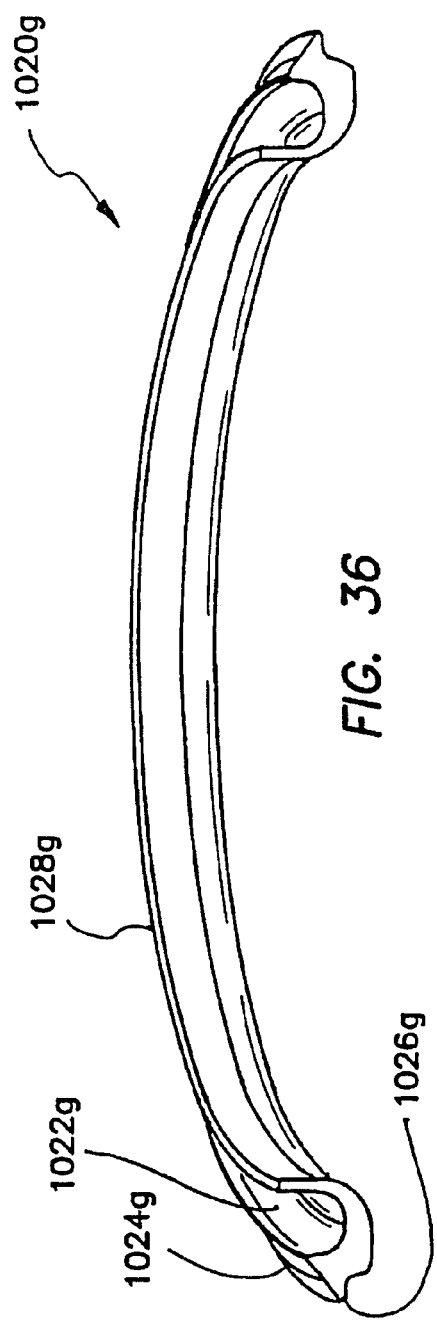

In another embodiment of the invention, FIGS. 33 and 34 illustrate a base 1020f having a smooth generally cylindrical inner surface 1022f, a rounded end surface 1024f, an annular lip 1026f, and an end surface 1028f having at least one toggle or latch 1029f sized and configured to fit a corresponding cap ring. In this embodiment, the toggle or latch 1029f operates to change the inner diameter of the cap ring to create a seal or release the cap ring from the base. In yet another embodiment of the invention, FIGS. 35 and 36 illustrate a base 1020g having a smooth generally cylindrical inner surface 1022g, a rounded end surface 1024g, an annular lip 1026g, and an end surface 1028g having a raised wall sized and configured to fit a corresponding cap ring.

An advantage associated with the modified surgical access device is it enables a surgeon to quickly retract and protectively line an abdominal wall incision while being able to easily accommodate variations from patient to patient in the thickness of the abdominal wall. In addition, the device effectively seals around the interior and exterior of the incision, and allows a sealing cap to be attached to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of preferred embodiments.

The invention claimed is:

1. An adjustable wound retractor adapted to dilate a surgical wound incision to a desired diameter, comprising:
    an inner ring having a diameter greater than the desired diameter of the wound incision and being adapted for disposition interiorly of the wound incision;
    an outer ring having an annular axis, a diameter greater than the desired diameter of the wound incision and being adapted for disposition exteriorly of the wound incision, and a lumen having tubing wall;
    a rod placed inside the lumen to deflect against the tubing wall to provide an audible signal to a user as the outer ring is rolled or turned over itself; and
    a flexible sleeve disposed in a generally cylindrical form between the inner ring and the outer ring,
    wherein the outer ring may be rolled over itself and around the annular axis to provide the sleeve with a radial retraction force sufficient to stretch the incision to the desired diameter.

2. The wound retractor of claim 1, wherein the rod is a stainless steel wire.

3. The wound retractor of claim 1, wherein the rod further provides retraction stability to the wound retractor.

4. The wound retractor of claim 1, wherein the lumen has a fan shape cross-section.

5. The wound retractor of claim 4, wherein the rod has a fan cross-section and is coaxially placed inside the lumen to serve as an incremental rotating mechanism of the wound retractor.

6. The wound retractor of claim 1, wherein each of the tubing wall and the rod includes a plurality of alignment points that operate to index and match each other as the outer ring is rolled out of and into alignment with respect to the rod.

7. The wound retractor of claim 1, wherein each of the tubing wall and the rod includes at least one alignment point providing indexing and incremental rotation of the outer ring.

8. The wound retractor of claim 1, wherein the rod has a cross-sectional shape including one of a solid rectangular shape, hollow rectangular shape, solid circular shape, hollow circular shape, and any solid or hollow geometric shape.

9. An adjustable wound retractor adapted to dilate a surgical wound incision to a desired diameter, comprising:
    an inner ring having a diameter greater than the desired diameter of the wound incision and being adapted for disposition interiorly of the wound incision;

an outer ring having an annular axis, a diameter greater than the desired diameter of the wound incision and being adapted for disposition exteriorly of the wound incision, and a lumen having tubing wall;

a flexible sleeve disposed in a generally cylindrical form between the inner ring and the outer ring; and a unidirectional mechanism for retaining the outer ring at one of a plurality of positions in order to provide a desired radial retraction force associated with that position, wherein the outer ring may be rolled over itself and around the annular axis to provide the sleeve with a radial retraction force sufficient to stretch the incision to the desired diameter.

10. The wound retractor of claim 9, wherein the unidirectional mechanism includes a one-way roller.

11. An adjustable wound retractor adapted to dilate a surgical wound incision to a desired diameter, comprising:

an inner ring having a diameter greater than the desired diameter of the wound incision and being adapted for disposition interiorly of the wound incision;

an outer ring having an annular axis, a diameter greater than the desired diameter of the wound incision and being adapted for disposition exteriorly of the wound incision, a generally prolate cross-section, and at least one lumen having tubing wall;

a rod placed inside the lumen to deflect against the tubing wall to provide an audible signal to a user as the outer ring is rolled or turned over itself; and a flexible sleeve disposed in a generally cylindrical form between the inner ring and the outer ring, wherein the outer ring may be rolled over itself and around the annular axis to provide the sleeve with a radial retraction force sufficient to stretch the incision to the desired diameter.

12. The wound retractor of claim 11, wherein the rod has a cross-sectional shape including one of a solid rectangular shape, hollow rectangular shape, solid circular shape, hollow circular shape, and any solid or hollow geometric shape.

13. An adjustable wound retractor adapted to dilate a surgical wound incision to a desired diameter, comprising:

an inner ring having a diameter greater than the desired diameter of the wound incision and being adapted for disposition interiorly of the wound incision;

an outer ring having an annular axis, a diameter greater than the desired diameter of the wound incision and being adapted for disposition exteriorly of the wound incision, a generally oblate cross-section, and at least one lumen having tubing wall;

a rod placed inside the lumen to deflect against the tubing wall to provide an audible signal to a user as the outer ring is rolled or turned over itself; and a flexible sleeve disposed in a generally cylindrical form between the inner ring and the outer ring, wherein the outer ring may be rolled over itself and around the annular axis to provide the sleeve with a radial retraction force sufficient to stretch the incision to the desired diameter.

14. The wound retractor of claim 13, wherein the rod has a cross-sectional shape including one of a solid rectangular shape, hollow rectangular shape, solid circular shape, hollow circular shape, and any solid or hollow geometric shape.

15. A surgical access device facilitating a sealing relationship with an instrument extending through the device and into an incision, the access device comprising:

an inner ring being adapted for disposition interiorly of the incision;

an outer ring having an annular axis and being adapted for disposition exteriorly of the incision;

a flexible sleeve connecting the inner ring and the outer ring and having properties to roll over itself and around the annular axis to shorten the sleeve in predetermined increments; and a valve structure disposed relative to the incision to securely receive the outer ring.

16. The surgical access device of claim 15, wherein the rolling properties of the outer ring provide the sleeve with a radial retraction force sufficient to stretch the incision to a desired diameter.

17. The surgical access device of claim 15, wherein the valve structure comprises a gel cap and an abdominal base.

18. The surgical access device of claim 17, wherein the gel cap further comprises a gel pad and a circumferential cap ring.

19. The surgical access device of claim 18, wherein the cap ring has an annular void on an inner circumference to form a sealing relationship with the abdominal base.

20. The surgical access device of claim 17, wherein the abdominal base comprises a rounded end surface along its inner diameter to secure the outer ring.

21. The surgical access device of claim 17, wherein the abdominal base comprises a plurality of toggles along its inner diameter to create a seal with the cap or to release the base from the cap.

22. The surgical access device of claim 17, wherein the abdominal base comprises a plurality of latches along its inner diameter to create a seal with the cap or to release the base from the cap.

23. The surgical access device of claim 17, wherein the abdominal base comprises a mating means along its inner diameter to create a seal with the cap or to release the base from the cap.

24. The surgical access device of claim 17, wherein the abdominal base comprises a raised wall along its inner diameter to fit a corresponding cap ring.

25. The surgical access device of claim 15, wherein the valve structure forms a pad adapted to be disposed over the incision and forms a seal around the incision, the pad includes a gel material having portions defining an access channel through the pad and extending into communication with the incision.

26. An adjustable wound retractor adapted to dilate a surgical wound incision to a desired diameter, comprising:

an inner ring having a diameter greater than the desired diameter of the wound incision and being adapted for disposition interiorly of the wound incision;

an outer ring having an annular axis and a diameter greater than the desired diameter of the wound incision and being adapted for disposition exteriorly of the wound incision, wherein the outer ring is formed from at least two generally circular tubes providing different annular lock points around the annular axis, each of the tubes is solid or includes a lumen having tubing wall, and the outer ring may be rolled over itself and around the annular axis to provide the sleeve with a radial retraction force sufficient to stretch the incision to the desired diameter;

a flexible sleeve disposed in a generally cylindrical form between the inner ring and the outer ring; and a rod placed inside at least one of the lumen of the tubes to deflect against the tubing wall to provide an audible signal to a user as the outer ring is rotated.

27. An adjustable wound retractor adapted to dilate a surgical wound incision to a desired diameter, comprising:
- an inner ring having a diameter greater than the desired diameter of the wound incision and being adapted for disposition interiorly of the wound incision;
- an outer ring having an annular axis and a diameter greater than the desired diameter of the wound incision and being adapted for disposition exteriorly of the wound incision;
- a flexible sleeve disposed in a generally cylindrical form between the inner ring and the outer ring, wherein
  - the outer ring comprises a double-tube joined by a web,
  - the outer ring may be rolled over itself and around the annular axis to provide the sleeve with a radial retraction force sufficient to stretch the incision to the desired diameter, each of the tubes of the double-tube is circular, and
  - each of the tubes of the double-tube is solid or includes a lumen; and
- a wire positioned in at least one of the lumens of the double tube.

28. The wound retractor of claim 27, wherein a wire is positioned in each of the lumens of the double tube.

29. An adjustable wound retractor adapted to dilate a surgical wound incision to a desired diameter, comprising:
- an inner ring having a diameter greater than the desired diameter of the wound incision and being adapted for disposition interiorly of the wound incision;
- an outer ring having an annular axis and a diameter greater than the desired diameter of the wound incision and being adapted for disposition exteriorly of the wound incision;
- a flexible sleeve disposed in a generally cylindrical form between the inner ring and the outer ring, wherein
  - the outer ring comprises a double-tube joined by a web,
  - the outer ring may be rolled over itself and around the annular axis to provide the sleeve with a radial retraction force sufficient to stretch the incision to the desired diameter, each of the tubes of the double-tube is circular, and
  - each of the tubes of the double-tube is solid or includes a lumen; and
- a rod positioned in at least one of the lumens of the double tube.

30. The wound retractor of claim 29, the rod having a cross-sectional shape including one of a solid rectangular shape, hollow rectangular shape, solid circular shape, hollow circular shape, and any solid or hollow geometric shape.

* * * * *